(12) United States Patent
Lopez

(10) Patent No.: US 11,779,757 B2
(45) Date of Patent: Oct. 10, 2023

(54) MRI-COMPATIBLE IMPLANTABLE MEDICAL DEVICES

(71) Applicant: Advanced Neuromodulation Systems, Inc., Plano, TX (US)

(72) Inventor: Matthew Lopez, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 180 days.

(21) Appl. No.: 17/382,294

(22) Filed: Jul. 21, 2021

(65) Prior Publication Data
US 2023/0028065 A1    Jan. 26, 2023

(51) Int. Cl.
*A61N 1/08* (2006.01)
*A61N 1/36* (2006.01)

(52) U.S. Cl.
CPC ......... *A61N 1/086* (2017.08); *A61N 1/36062* (2017.08); *A61N 1/36114* (2013.01)

(58) Field of Classification Search
CPC .............. A61N 1/086; A61N 1/36062; A61N 1/36114; A61N 1/08
See application file for complete search history.

(56) References Cited

U.S. PATENT DOCUMENTS

| | | | |
|---|---|---|---|
| 9,302,101 B2 | 4/2016 | Wahlstrand et al. | |
| 9,492,651 B2 | 11/2016 | Bottomley et al. | |
| 2009/0163981 A1* | 6/2009 | Stevenson | A61N 1/3605 607/63 |
| 2010/0114281 A1 | 5/2010 | Swoyer | |
| 2021/0128919 A1* | 5/2021 | Zellmer | A61F 2/446 |
| 2022/0111209 A1* | 4/2022 | Madabhushi | A61N 1/36125 |

\* cited by examiner

*Primary Examiner* — Paula J Stice
(74) *Attorney, Agent, or Firm* — Norton Rose Fulbright US LLP

(57) ABSTRACT

One or more antennas are electrically coupled to one or more switches of an implantable medical device (IMD) in which the one or more switches are additionally electrically coupled to one or more lead wires of an IMD lead. The one or more switches also are electrically coupled to one or more electrodes or electrical circuitry of the IMD's implantable pulse generator (IPG). In response to exposure of the IMD to an energetic electromagnetic field, a voltage signal is induced in the one or more antennas and provided, possibly via one more filters, as a control signal to the one or more switches. Receipt of the control signal by the one or more switches automatically configures the one or more switches into a non-conductive state, thereby electrically isolating the one or more lead wires from the one or more electrodes or the IPG electrical circuitry.

18 Claims, 13 Drawing Sheets

MRI-COMPATIBLE IMPLANTABLE MEDICAL DEVICES

TECHNICAL FIELD

The present invention relates generally to implantable medical devices (IMDs) configurable for safe operation in external signal environments, such as within the magnetic and radio frequency (RF) fields generated by operation of magnetic resonance imaging (MM) devices.

BACKGROUND OF THE INVENTION

Implantable medical devices (IMDs) providing functions such as stimulation of muscle or neurological tissue and/or sensing of physiological occurrences within a human body are used for a wide variety of medical conditions. For example, IMDs in the form of implantable electrical stimulation devices have been commercially distributed that allow electrical pulses or signals to be controllably delivered to a targeted tissue or nerves after implantation of the respective device within a patient. Such implantable electrical stimulation devices may be used for cardiac pace making, cardiac rhythm management, treatments for congestive heart failure, implanted defibrillators, and neurostimulation. Neurostimulation encompasses a wide range of applications, such as for example, pain control, nervous tremor mitigation, incontinence treatment, epilepsy seizure reduction, and vagus nerve stimulation for clinical depression.

Implantable electrical stimulation devices generally include an implanted pulse generator (IPG) that generates electrical pulses or signals that are transmitted to a targeted tissue or nerves through a therapy delivery element, such as a lead having electrodes. The therapy delivery element is generally precisely placed within the patient's body to achieve therapeutic efficacy or reduced side effects. For example, whether used in a stimulation and/or sensing capacity, therapy delivery elements in the form of leads are commonly implanted along peripheral nerves, within the epidural or intrathecal space of the spinal column, and around the heart, brain, or other organs or tissue of a patient. Once implanted, the lead extends from the stimulation/sensing site to the location of the implantable electrical stimulation device. The distance from the stimulation/sensing site to the IMD may, for example, be on the order of 20-100 cm. In some situations, a lead extension may be utilized between a lead and IMD to span relatively long distances.

Leads configured for use with IMDs, such as implantable electrical stimulation devices, typically include a connector apparatus (e.g., one or more electrical contacts) disposed on a proximal end and the aforementioned electrodes (e.g., one or more electrically conductive rings, split or non-continuous rings, etc.) disposed on a distal end. Conductive wires (e.g., filars formed from stranded or solid core insulated conductors) interconnect the electrodes at the distal end to corresponding contacts of the connector apparatus at a proximal end. A jacket (e.g., a flexible, resilient member formed biocompatible polymer) is typically included in the body of leads, wherein the conductive wires may be disposed within the jacket and protected from body tissue and other external agents by the jacket.

Once implanted within the body of a patient, IMDs and their associated leads may be exposed to various external signal environments. For example, the patient may be subject to metal detector scans and/or backscatter imaging, such as when passing through security checkpoints, which creates an environment of electromagnetic radiation in which the IMD and lead(s) are present. As another example, a magnetic resonance imaging (MRI) scan may be performed with respect to the patient, whereby the IMD and associated lead(s) may be within the electromagnetic radiation (e.g., magnetic and radio frequency (RF) fields) generated by the Mill device.

Although the jacket of a lead may provide physical protection of the wires within, the jacket typically provides little to no protection with respect to electromagnetic radiation. The wires may, however, be of sufficient length to resonate or otherwise respond electrically to various forms of electromagnetic radiation. For example, electromagnetic radiation in the RF spectrum may induce voltages and/or currents into the wires, whereby voltage and/or current may unintentionally be introduced at one or more electrodes of the lead.

The electromagnetic radiation of various external signal environments may pose a risk to tissue in proximity to the lead electrodes. For example, where the intensity of the electromagnetic radiation is relatively high, tissue in contact with an electrode having voltage and/or current induced into a wire connected thereto may be exposed to excessive voltage and/or current causing heating (e.g., burning) and/or other undesired effects, a process typically referred to as localized temperature rise. Although the level of electromagnetic radiation encountered in general daily experience is typically at a level unlikely to cause undesired effects, various external signal environments may nevertheless provide electromagnetic radiation at levels sufficient to cause undesired, even dangerous, effects. For example, if the patient is exposed to electromagnetic radiation from a MRI scan, voltage and/or current may be induced into the wires sufficient to cause tissue damage at the area of the electrodes due to heating of tissue proximate to the electrodes. Such tissue damage, particularly damage to neurological tissue, may be dangerous to the patient.

Further, voltage and/or current induced within the wires of the lead may leak into electronics of the IPG thereby causing damage to the IPG, a process typically referred to as injection. Damage to the IPG may negatively impinge upon the operation of the IMD. Alternatively, an induced voltage and/or current of a sufficient magnitude provided to IPG electronics may cause the IMD to cease functioning altogether.

In light of the foregoing, leads for implantable electrical stimulation devices have begun to be configured for compatibility for use in situations where they may be exposed to a source of high-power and/or energetic electromagnetic radiation. For example, a lead may be configured for shielding from electromagnetic radiation emitted by MM devices using a conductive material (e.g., tantalum braid) embedded within the jacket or other outer sheath of the lead (e.g., within or surrounded by insulating material forming the lead body). Such shielded lead configurations often, however, introduce disadvantages with respect to the flexibility and lead life (e.g., prone to damage due to compressive forces applied by a lead anchor, kinking during handling, etc.). In another example, a lead may be configured to mitigate the effects of voltages and/or currents induced into the wires thereof through relatively high impedance implementations of one or more conductive aspects (e.g., the wires and/or electrodes) of the lead. Such high impedance configurations generally result in reduced battery life of the implantable electrical stimulation device (e.g., necessitating higher stimulation signals to be used).

Additionally, IMDs may be configured to be placed in a MM safe mode by a medical practitioner before a patient receives a MRI scan. For example, an IPG of the IMD may include a switch that the medical practitioner can activate to electrically isolate the IPG electronics from one or more lead wires of the lead to prevent induced injection voltage and/or current from entering the IPG electronics during performance of the MRI scan. However, the medical practitioner may forget to activate the switch to place the IMD in the MM safe mode. Additionally, a biasing voltage provided to the switch by a battery, usually positioned with the IPG, causes the switch to become non-conductive and thus places the IMD in the MRI safe mode. However, due to repeated operation of the IPG and/or natural decay of the battery, the battery may be unable to generate sufficient voltage to bias the switch into a non-conductive state. Accordingly, even though the medical practitioner has placed the IMD in the MRI safe mode, the switch remains conductive and voltage and/or current induced in one or more lead wires by energetic electromagnetic radiation, such as produced during performance of an MM scan, may pass through the one or more lead wires into the IPG electronics, causing damage to the IPG.

Moreover, as MM devices are deployed that utilize higher energy densities to produce medical images with higher resolution, it is likely that electromagnetic shielding will be unhelpful in mitigating or preventing this induced leakage voltage and/or current. For example, currently, MRI devices generate electromagnetic radiation having energy densities between 2 W/kg and 12 W/kg (e.g., 2-4 W/kg for 15 minute exposure averaged for whole body MRIs, 3 W/kg for 10 minute exposure averaged for head MRIs, 8 W/kg for 5 minute exposure averaged for head or torso MRIs, 12 W/kg for 5 minute exposure averaged for extremity MRIs). However, it is expected that MRI devices soon will generate electromagnetic radiation having energy densities significantly higher than the 2 W/kg-12 W/kg range discussed above. These higher energy density MRI scans are likely to increase the risk of damage to tissue surrounding the IMD and to the IMD itself due to localized temperature rises and injection, respectively.

BRIEF SUMMARY OF THE INVENTION

Disclosed are implementations for electrically isolating one or more components of an implantable medical device (IMD) from one or more lead wires of a lead of the IMD when the IMD is exposed to energetic electromagnetic radiation, such as electromagnetic radiation generated through operation of a medical resonance imaging (MRI) device. Energetic electromagnetic radiation, such as produced by operation of a MM device, can induce a voltage and/or current in the one or more lead wires. This voltage and/or current can propagate through the one or more lead wires into electrodes, where it can heat tissue surrounding the electrodes, thereby potentially damaging the tissue. Additionally, the voltage and/or current can propagate through one or more lead wires into electrical circuitry of an implantable pulse generator (IPG) of the IMD, potentially damaging the IPG and compromising its functional integrity.

To mitigate the harmful effects of voltage and/or current induced in lead wires when in the presence of energetic electromagnetic radiation, one or more antennas may be provided. The one or more antennas may be excited by the same electromagnetic radiation as induces a voltage and/or current in the lead wires, thereby causing a voltage signal to be propagated within the one or more antennas. The voltage signal induced by the one or more antennas may be used as a control signal. The voltage signal may be provided to one or more filters, such as resistor capacitor (RC) filters, where the voltage signal can be processed into a continuous and relatively smooth signal, thereby providing a more consistent control signal level. The control signal can be provided to one or more switches electrically coupled to the one or more antennas. The one or more switches are configurable between a conductive state and a non-conductive state based on the control signal. For example, in the conductive state, the switch(es) may couple one or more lead wires to electrodes used to deliver stimulation therapy to the patient or to couple the lead wire(s) to the IPG. In the non-conductive state the switch(es) may electrically isolate the one or more lead wires from the electrodes and/or electrical circuitry of the IPG. By electrically isolating the one or more lead wires from the electrodes and/or electrical circuitry of the IPG, the voltage and/or current induced in the one or more lead wires by the energetic electromagnetic radiation cannot propagate into the electrode(s) or electrical circuitry of the IPG from the one or more lead wires.

When exposure of the IMD to the energetic electromagnetic radiation ceases, because, for example, a patient in whom the IMD is implanted has completed a MRI session, the voltage induced at the one or more antennas of the IMD ceases. Accordingly, no control signal is provided to the one or more switches of the IMD, and the one or more switches reenter the conductive state, thereby electrically coupling the one or more lead wires of the lead to the electrode(s) or electrical circuitry of the IPG. Accordingly, during an electrostimulation therapy session, electrical pulses generated by the IPG can propagate through the one or more lead wires to one or more electrodes to provide electrostimulation therapy to the patient.

In accordance with an aspect of the disclosure, an apparatus includes a lead having a lead wire and an electrode. Additionally, the apparatus includes an antenna configured to generate a control signal in response to excitation of the antenna by a MM device. Moreover the apparatus includes a switch electrically coupled to the antenna and configured to electrically isolate the electrode from the lead wire in response to the control signal.

In an additional aspect of the disclosure, an IMD includes a lead having at least one lead wire and an antenna configured to generate a control signal in response to excitation of the antenna by a MM device. The IMD further incudes an IPG having electrical circuitry coupled to the lead. The IPG includes a switch electrically coupled to the antenna of the lead and configured to electrically isolate the electrical circuitry of the IPG from the at least one lead wire in response to the control signal.

In yet another aspect of the disclosure, an IMD includes a lead having a lead wire and an electrode. Additionally, the lead incudes a first antenna configured to generate a first control signal in response to excitation of the first antenna by a MRI device and a first switch electrically coupled to the first antenna and configured to electrically isolate the electrode from the lead wire in response to the first control signal. Electrical isolation of the electrode from the first lead wire is configured to prevent a first injection voltage induced in the lead by the MRI device from entering the electrode. The IMD also includes an IPG having electrical circuitry in electrical communication with the lead wire. A second antenna is configured to generate a second control signal in response to excitation of the second antenna by the MRI device. Additionally, the IMD includes a second switch electrically coupled to the second antenna and configured to electrically couple or isolate the electrical circuitry of the IPG electronics from the lead wire in response to the second control signal. Electrical isolation of the IPG electronics from the lead wire is configured to prevent injection voltage induced in the lead wires by the MRI device from entering the electrical circuitry of the IPG electronics.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE INVENTION

Figure 1:
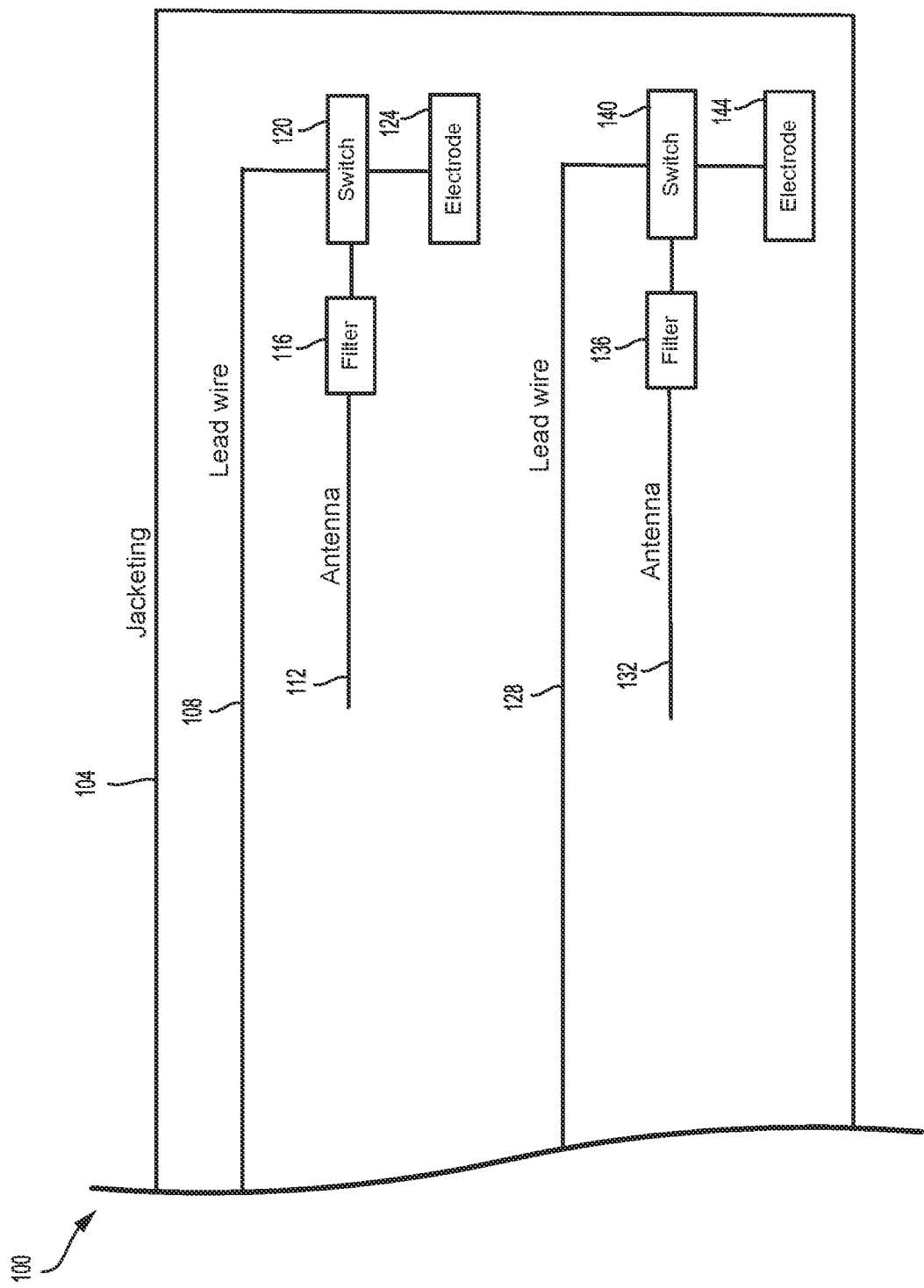
FIG. 1 shows a block diagram illustrating aspects of an apparatus according to embodiments of the present disclosure.

Referring to FIG. 1, a block diagram illustrating aspects of an MRI compatible lead for an IMD according to the present disclosure is shown as lead 100. Lead 100 may be configured to couple to an IMD to facilitate delivery of neurostimulation therapy to a patient. Lead 100 is an MM compatible lead that is configured to electrically isolate one or more electrodes from one or more lead wires to prevent electric current and/or voltage from propagating into the one or more electrodes in response to exposure of lead 100 to energetic electromagnetic radiation, such as generated by operation of an MRI device.

As shown in FIG. 1, lead 100 includes lead wire 108 and electrode 124. Lead 100 may be coupled to an implantable pulse generator (IPG) (not depicted in FIG. 1). The IPG may be configured to deliver electric pulses and/or signals to the patient via lead wire 108 and electrode 124. More specifically, electrode 124 may be disposed at a treatment site positioned within a body of the patient, such as within the patient's spinal cord, brain, heart, and/or other organ systems, and the electrical pulses or signals may be provided as part of a neurostimulation therapy for the patient (e.g., to treat pain, a movement disorder, or another condition of the patient). Lead 100 may be surrounded by insulating jacket 104 formed from a biocompatible insulating material (e.g., a biocompatible insulating polymer). In some aspects, space surrounding lead wire 108 or other internal components of lead 100 may be filled with a dielectric material.

Additionally, lead 100 includes antenna 112 configured to generate a control signal in response to excitation of antenna 112 (e.g., by energetic electromagnetic radiation emitted by a source such as by operation of a MRI device). Switch 120 is electrically coupled to antenna 112. In some aspects, switch 120 may be a solid state switch. For example, switch 120 may include one or more metal oxide semiconductor field effect transistors (MOSFETs). Additional exemplary aspects of the structure of switch 120 are described in more detail below with reference to FIG. 2. Switch 120 is configurable between a conductive state and a non-conductive state based on the control signal generated by antenna 112. In the conductive state, switch 120 may electrically couple lead wire 108 to electrode 124, thereby enabling stimulation therapy to be delivered to the patient. In the non-conductive state, switch 120 may electrically isolate the lead wire 108 from electrode 124. By electrically isolating lead wire 108 from electrode 124, the voltage and/or current induced in lead wire 108 by the energetic electromagnetic radiation cannot propagate into electrode 124, thereby preventing tissue surrounding the electrodes from being heated by the induced voltage or current, which could potentially damage the tissue surrounding electrode 124 or otherwise create discomfort for the patient.

In some aspects, filter 116 may be positioned between antenna 112 and switch 120. Filter 116 may be configured to process the control signal generated by antenna 112, such as to smoothen the control signal and/or control a voltage provided by the control signal. Filter 116 may be a resistor capacitor (RC) filter or other averaging filter configured to linearize a voltage corresponding to the first control signal. In other aspects, filter 116 may be a passive suppression filter configured to attenuate a specific range of radio frequencies. For example, a passive suppression filter may be configured to attenuate non-MRI frequencies so that only radio frequencies or energy induced and/or emitted by operation of an energetic electromagnetic radiation source, such as operation of a MRI device, trigger generation of the control signal used to transition the switches between the conductive and non-conductive states.

As briefly described above, the control signal generated by antenna 112 may be provided to switch 120. Switch 120 may be configured to transition between the conductive state and the non-conductive state based on the control signal generated by antenna 112. For example, when lead 100 is in the presence of energetic electromagnetic radiation, such as generated by a MRI device, a voltage or current is induced at antenna 112, which may be provided as a control signal to switch 120. When provided, the control signal may transition switch 120 to the non-conductive state, thereby preventing a voltage and/or electric current induced in one or more lead wires of lead 100 (e.g., lead wire 108) by the energetic electromagnetic radiation from entering electrode 124 via switch 120 and lead wire 108. Accordingly, since electrode 124 does not receive the induced voltage and/or electric current, tissue around electrode 124 will not be damaged while lead 100 is in the presence of the energetic electromagnetic radiation, such as when a patient in whom lead 100 is implanted undergoes a MRI procedure or other medical procedure that might generate energetic electromagnetic radiation.

When an excitation source ceases to generate energetic electromagnetic radiation, such as when a MRI procedure is complete, antenna 112 ceases to produce the control signal. In response to the control signal ceasing to be provided to switch 120 by antenna 112, switch 120 transitions to the conductive state, thereby permitting voltage and/or electric current to propagate from lead wire 108 to electrode 124 via switch 120. In this manner and as an example, after conclusion of a MM procedure, the IMD may continue to operate as it did prior to performance of the MM procedure. To elaborate, once the IMD is no longer exposed to the energetic electromagnetic radiation, switch 120 automatically transitions to the conductive state, since antenna 112 no longer is excited by energetic electromagnetic radiation and thus ceases generation of the first control signal. Therefore, voltage and/or current can propagate from the IPG (not depicted in FIG. 1) through lead wire 108 to electrode 124 via switch 120. In this manner, the IMD can continue to provide electrostimulation therapy to the patient.

Although FIG. 1 depicts antenna 112, in some implementations, a failover antenna (not shown) may also be provided and coupled to switch 120. Such a failover antenna may be configured to generate and provide a redundant control signal to switch 120 in response to excitation of the failover antenna by energetic electromagnetic radiation, such as generated by the MRI device, thereby providing redundancy with respect to controlling the transition of switch 120 between the conductive and non-conductive states. Thus, if antenna 112 or the failover antenna is damaged or ceases to function, the control signal may still be provided to switch 120 by the other antenna when lead 100 is in the presence of electromagnetic radiation. Examples of systems incorporating a failover antenna are described in more detail below with reference to FIG. 6.

In some implementations, lead 100 may include a plurality of lead wires, a plurality of electrodes, a plurality of switches, and a plurality of antennas. Each switch of the plurality of switches may be electrically coupled to an antenna of the plurality of antennas. Each switch of the plurality of switches may also be configured to electrically couple or isolate an electrode of the plurality of electrodes to or from a lead wire of the plurality of lead wires in response to a control signal generated at a corresponding antenna of the plurality of antennas.

For example, as depicted in FIG. 1, lead 100 is shown to include lead wire 128, switch 140, electrode 144, filter 136 and antenna 132. Switch 140 is electrically coupled to electrode 144 and antenna 132. Antenna 132 may operate in a manner similar to antenna 112 described above. For example, excitation of antenna 132 by energetic electromagnetic radiation, such as generated by a MM device, causes antenna 132 to generate a control signal that may be provided to switch 140. Receipt, by switch 140, of the control signal from antenna 132 causes switch 140 to enter the non-conductive state, thereby electrically isolating electrode 144 from lead wire 128 so that voltage and/or electric current induced by the energetic electromagnetic radiation (e.g., by operation of the MRI device) does not enter into electrode 144. As with antenna 112 and switch 120, when an excitation source, such as a source of electromagnetic radiation, ceases to be present (e.g., because a MRI procedure being performed on a patient in whom lead 100 is implanted has ended) switch 140 is configured to automatically return to the conductive state in which electrostimulation therapy may be performed via lead wires 108, 128 and electrodes 124, 144. In an implementation, filter 136 may be positioned between antenna 132 and switch 140. Like filter 116, filter 136 and may be a RC filter or other averaging filter configured to convert a rapidly changing high frequency waveform into a smooth, approximately linear waveform. Filters 116, 136 may be configured to linearize an input voltage corresponding to the second control signal, as explained more fully with reference to FIG. 10.

Figure 7:
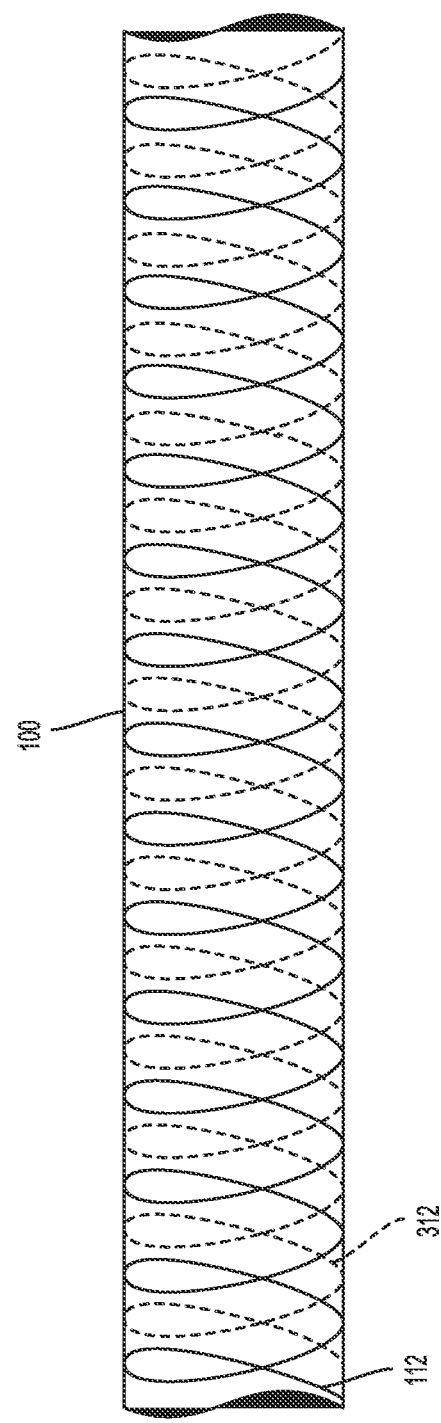
FIG. 7 shows a block diagram illustrating aspects of a lead antenna according to embodiments of the present disclosure.
Figure 8:
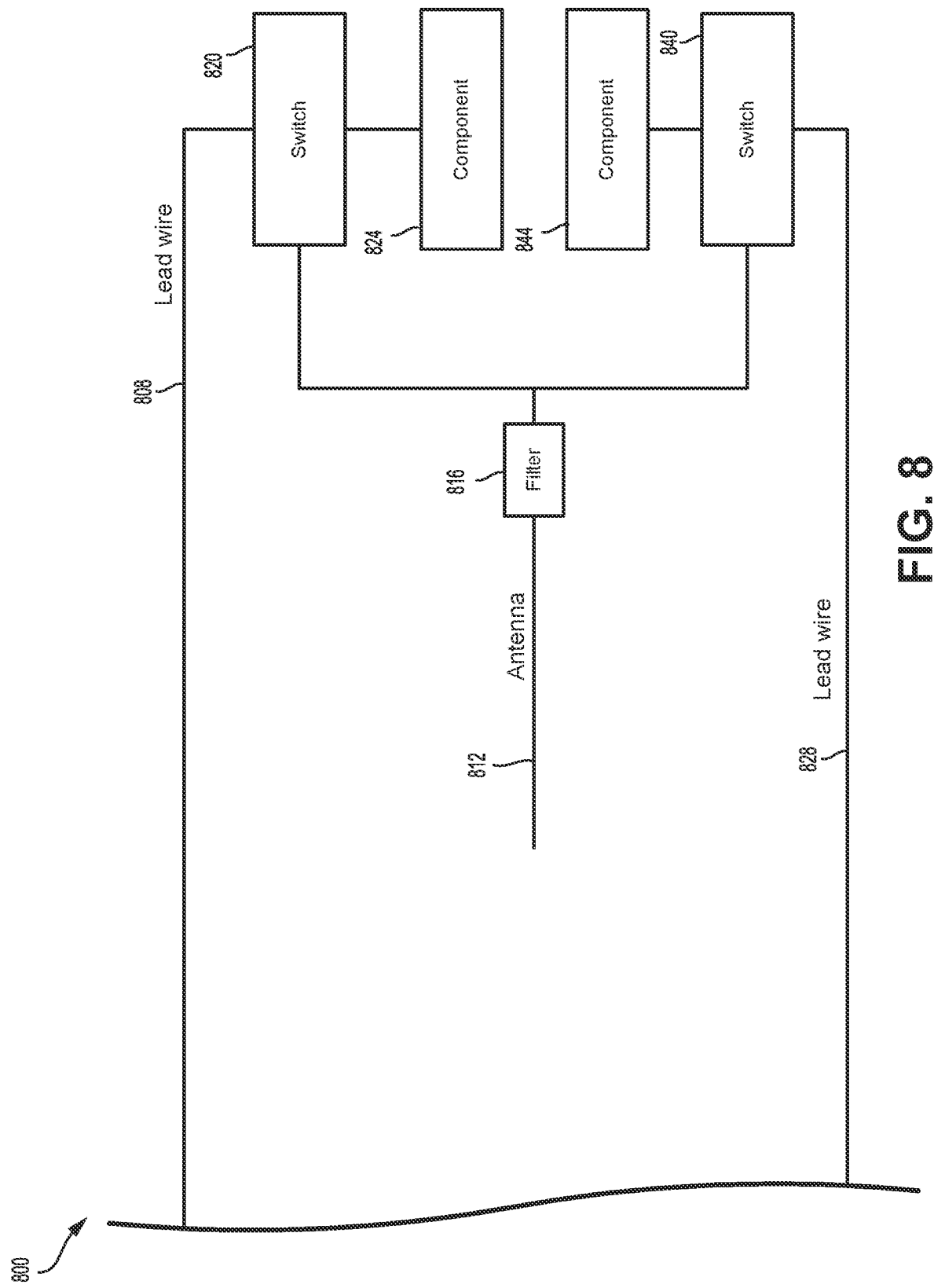
FIG. 8 shows a block diagram illustrating additional aspects of an apparatus according to embodiments of the present disclosure.

It is noted that although FIG. 1 depicts switch 120 as receiving the control signal from antenna 112 and switch 140 as receiving the control signal from antenna 132, in some implementations and as explained more fully with reference to FIG. 8, switches 120, 140 may be electrically coupled to a single antenna (e.g., antenna 112 or antenna 132). It is also noted that while FIG. 1 illustrates the plurality of lead wires as including two lead wires (e.g., lead wires 108, 128) and the plurality of electrodes as including two electrodes (e.g., electrodes 124, 144), leads according to the present disclosure may include a single lead wire/electrode pair or include more than two lead wire/electrode pairs if desired (e.g., by incorporating additional antennas and switches configured as shown in FIG. 1). Moreover, while FIG. 1 illustrates lead 100 as including an antenna/switch pair for each lead wire/electrode pair, some embodiments of the present disclosure may utilize alternative antenna/switch arrangements to control electrical isolation of lead wire/ electrode pairs, as described in more detail below with reference to FIGS. 6-9.

The antennas of FIG. 1, such as antennas 112,132, may be fabricated from a conductive material. In some aspects, the material used to form antennas 112, 132 may have a higher conductivity than material from which the lead wires, such as lead wires 108,128, are fabricated. However, in other aspects, the material used to form antennas 112, 132 may have the same conductivity or a lower conductivity than material from which the lead wires, such as lead wires 108,128, are fabricated. In some aspects, antennas 112, 132 may have a same gauge, a smaller gauge, or a larger gauge than lead wires 108, 128. In some aspects, and as explained more fully with reference to FIG. 7, the antennas, such as antennas 112,132, may be helically wrapped to increase exposure of antennas 112,132 to energetic electromagnetic radiation, which may improve the ability of antennas 112, 132 to generate control signals in response to excitation of antennas 112, 132 by the electromagnetic radiation, as described above.

Additionally, electrodes (e.g., electrodes 124,144) included in the lead (e.g., lead 104) may be any type of electrodes. For instance, the electrodes may be paddle electrodes, needle and wire electrodes, electrocorticographic electrodes, electrode arrays, microelectrodes, or other types of electrodes. Moreover, in some embodiments the electrodes may be biphasic electrodes.

As MM devices become more powerful, attempts to utilize electromagnetic shielding to protect leads from electromagnetic radiation, as have been used in the past, are unlikely to adequately protect against voltages and/or currents induced in lead wires, thereby causing local tissue heating and potentially damaging tissue. As shown above, aspects of the present disclosure provide an automated technique for controlling electrical coupling and isolation of lead wires from electrodes when a lead is in the presence of electromagnetic radiation. The solution provided by lead 100 addresses the problems associated with higher power MRI scans by facilitating automated reconfiguration of the lead 100 between a therapeutic mode of operation and a MM-safe mode based on the presence of energetic electromagnetic radiation or lack thereof. In the therapeutic mode of operation, the switch(es) is placed into a conducive state to enable therapeutic operations via delivery of stimulation pulses to the electrode(s) via the lead wire(s) of lead 100. In the MM-safe mode, the switch(es) is placed into the non-conductive state to electrically isolate the electrode(s) from the lead wire(s), thereby preventing voltages and/or currents induced in the lead wire(s) from reaching the electrode(s). In this manner, heightened safety is provided without compromising operational integrity. It is to be understood that while primarily described with reference to electromagnetic radiation produced by a MM device, automatic triggering mechanisms for electrically isolating electrodes from lead wires according to the present disclosure may be utilized to protect patients in any environment where electromagnetic radiation is present at sufficient power and/or with sufficient energy to induce currents and/or voltages in lead wires and are not limited to use with electromagnetic radiation generated from operation of MRI devices.

Figure 2:
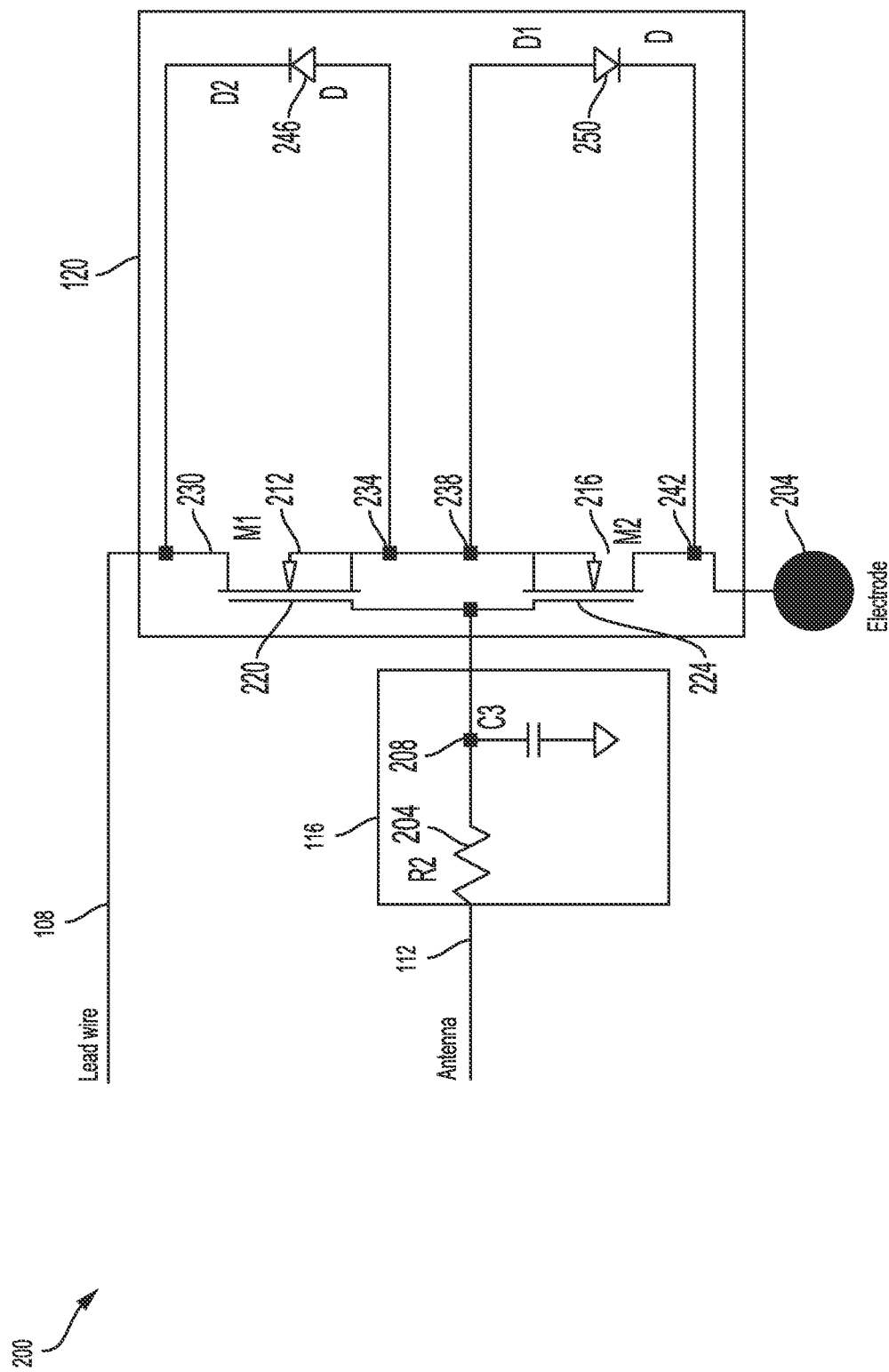
FIG. 2 shows a circuit diagram illustrating aspects of a MRI safe lead according to embodiments of the present disclosure.

Referring to FIG. 2, a circuit diagram illustrating aspects of a MM-safe lead according to the present disclosure is shown as a circuit 200. Circuit 200 includes switch 120, lead wire 108 electrically coupled to switch 120, and antenna 112 electrically coupled to switch 120 via filter 116. Switch 120 is a solid state switch configured to rapidly enter into the non-conductive state in response to receipt of the control signal from antenna 112, as described above with reference to FIG. 1. In this manner, switch 120 is configured to electrically isolate electrode 124 from lead wire 108 during exposure of an implantable medical device (IMD) to energetic electromagnetic radiation, such as emitted by operation of a MRI device.

Switch 120 includes first MOSFET 212 and second MOSFET 216 in a back-to-back configuration. First gate 220 of first MOSFET 212 and second gate 224 of second MOSFET 216, respectively, are coupled to antenna 112 via filter 116. First source 230 of first MOSFET 212 is coupled to lead wire 108. First drain 234 of first MOSFET 212 is coupled to second source 238 of second MOSFET 216. Second drain 242 of second MOSFET 216 is coupled to electrode 124. First diode 246 is coupled to first MOSFET 212 and second diode 250 is coupled to second MOSFET 216. First diode 246 has an opposite polarity to second diode 250. In implementations, first MOSFET 212 and second MOSFET 216 may be n-type depletion MOSFETs.

During operation in the absence of energetic electromagnetic radiation, voltage and/or current propagates from lead wire 108 to electrode 124 via first MOSFET 212 and second MOSFET 216 (e.g., from first source 230 of first MOSFET 212 to second drain 242 of second MOSFET 216). For example, an IPG of the IMD may generate an electric pulse and/or signal configured to propagate from lead wire 108 to electrode 124 via first MOSFET 212 and second MOSFET 216. Electrode 124 may be a bipolar electrode configured to provide biphasic pulses to tissue surrounding electrode 124 in which delivery of the biphasic pulses is effectuated via first diode 246 and second diode 250. As explained, however, with reference to FIG. 1, first electrode 124 may be any type of electrode.

In the presence of energetic electromagnetic radiation, such as when the IMD or the lead is exposed to an oscillating magnetic field of a MRI device, a voltage is induced in antenna 112 by the energetic electromagnetic radiation. As described above, voltage or current may be induced in antenna 112 and the induced voltage or current may be utilized to generate a control signal that is provided to first gate 220 of first MOSFET 212 and second gate 224 of second MOSFET 216, causing first MOSFET 212 and second MOSFET 216 to transition to the non-conductive state, thereby electrically isolating lead wire 108 from electrode 124. In this manner, voltage and/or current induced in lead wire 108 by the energetic electromagnetic radiation cannot pass into electrode 124. Since electrode 124 is electrically isolated from lead wire 108 and since voltage and/or current induced by the energetic electromagnetic radiation cannot propagate through switch 120, tissue surrounding electrode 124 is protected from heating (e.g., localized heating).

In some aspects, filter 116 may be positioned between antenna 112 and a node coupled to first gate 220 of first MOSFET 212 and second gate 224 of second MOSFET 216. In the circuit 200, filter 116 is shown as an RC filter that includes resistor 204 and capacitor 208. Filter 116 is configured to process a voltage or current induced in first antenna 112 by energetic electromagnetic radiation, such as generated by a MRI device, by linearizing and reducing variability in the voltage of the control signal.

Although the switches described with reference to circuit 200 of FIG. 2 are shown as n-type depletion MOSFETs, in alternative aspects p-type MOSFETs may be used. In such implementations, an inverter may be positioned between filter 116 and the gates of the p-type MOSFETs so that a control signal provided to the gates of the p-type MOSFETs is a low voltage signal (e.g., corresponding to zero volts) to cause the p-type MOSFETs to enter a non-conductive state in which electrode 124 is electrically isolated from lead wire 108. Additionally, although MOSFETs are described with respect to circuit 200, other types of switches, such as bipolar junction transistors (BJTs), can be used.

Figure 3:
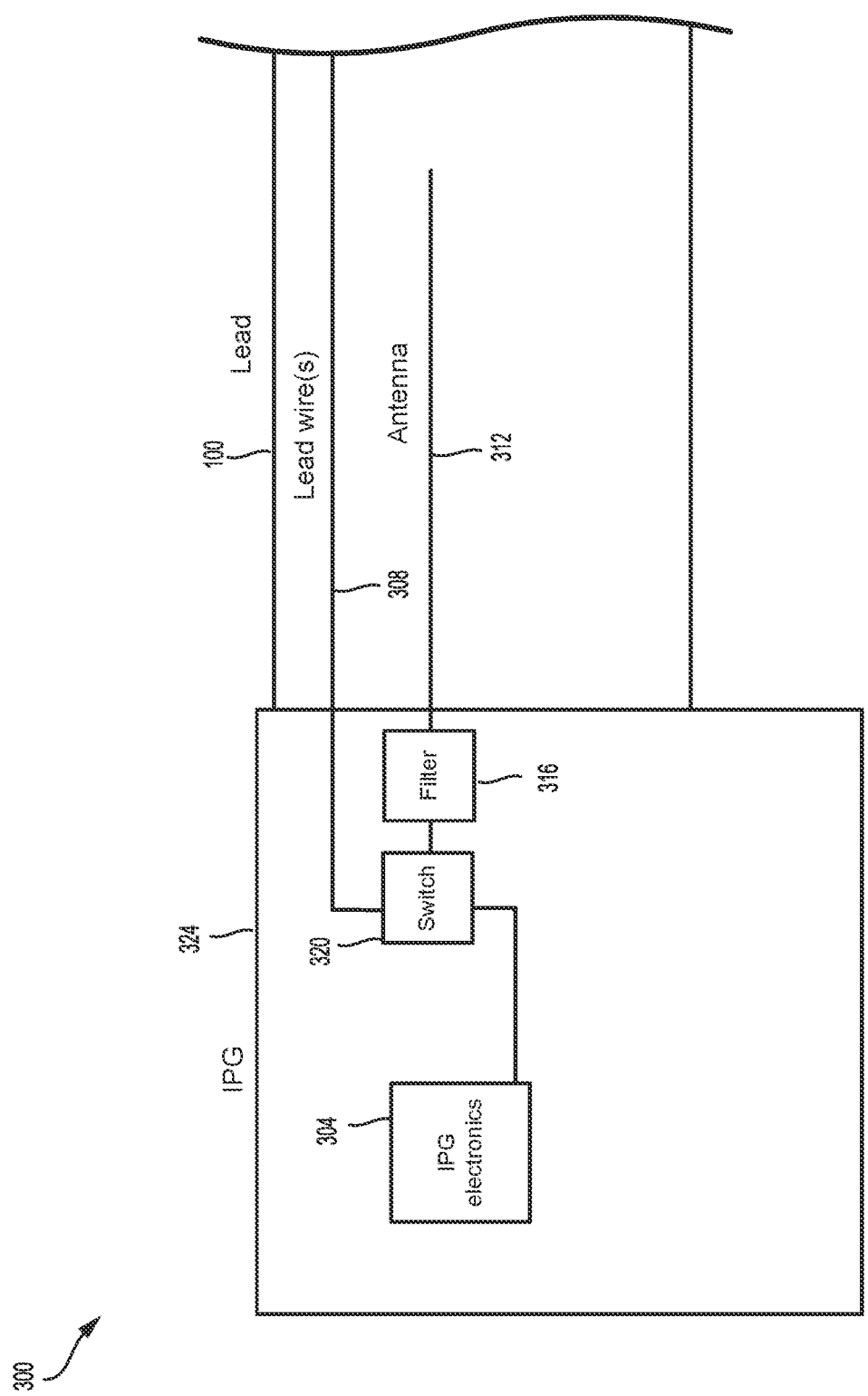
FIG. 3 shows a block diagram illustrating aspects of an IMD according to embodiments of the present disclosure.

Referring to FIG. 3, a block diagram illustrating aspects of an implantable medical device (IMD) according to the present disclosure is shown as IMD 300. IMD 300 is configured to provide electrostimulation therapy to a patient via lead 100 implanted within a patient's anatomy, such as to provide electrostimulation therapy to the patient's spine, heart, brain, and/or other anatomy or regions of the patient. For example, a proximal end of lead 100 may be coupled to the IMD 300, and electric pulses generated by an IPG 324 of the IMD 300 may travel through one or more lead wires 308 to one or more electrodes disposed at a distal end of lead 104 (not shown in FIG. 3) proximate the tissue to be stimulated. These electric pulses may mitigate one or more disorders, such as neurological disorders, cardiac disorders, pain, movement disorders, and the like. It is noted that one or more lead wires 308 may include one or more of lead wires 108, 128 of FIG. 1, which may be electrically coupled to one or more electrodes (e.g., electrodes 124, 144 of FIG. 1).

As shown in FIG. 3, lead 100 includes antenna 312 configured to generate a control signal in response to excitation of antenna 312 by a source of energetic electromagnetic radiation, such as is generated by operation of a MRI device. Moreover, IPG 324 includes electrical circuitry, referred to as IPG electronics 304, that may be in electrical communication with lead 100, and more specifically with one or more lead wires 308. As illustrated in FIG. 3, switch 320 may be electrically coupled to antenna 312 and configured to electrically isolate IPG electronics 304 from one or more lead wires 308 of lead 100 in response to the control signal provided by antenna 312. In some aspects, filter 316 is disposed between switch 320 and antenna 312. Filter 316 may be configured to process the control signal generated by antenna 312, such as to smoothen the control signal and/or control a voltage provided by the control signal. Filter 316 may be a RC filter or other averaging filter configured to linearize a voltage corresponding to the first control signal. In other aspects, filter 316 may be a passive suppression filter configured to attenuate a specific range of radio frequencies. For example, a passive suppression filter may be configured to attenuate non-MRI frequencies so that only radio frequencies or energy induced and/or emitted by operation of an energetic electromagnetic radiation source, such as operation of a MRI device, trigger generation of the control signal used to transition the switches between the conductive and non-conductive states.

During therapeutic operation, IPG electronics 304 may generate electric pulses and/or signals that travel through one or more lead wires 308 to one or more electrodes (not depicted in FIG. 3) to provide electrostimulation therapy to the patient. Exposure of IMD 300 to energetic electromagnetic radiation, such as when the patient undergoes a MM procedure, may induce an excitation signal, such as a voltage or current, in antenna 312. As described above, the induced voltage or current in antenna 312 may be provided as a control signal to switch 320. Upon receiving the control signal, switch 320 may transition to a non-conductive state in which IPG electronics 304 are electrically isolated from one or more lead wires 308. As explained above, a voltage or current induced in one or more lead wires 308 by energetic electromagnetic radiation may leak into IPG electronics 304 (i.e., a process referred to as injection), which may impair IPG electronics 304 or render IPG electronics 304 inoperable. Electrically isolating IPG electronics 304 from the one or more lead wires 308 may prevent an injection voltage (and/or a corresponding injection current) from being introduced to IPG electronics 304, thereby preventing damage to IPG electronics 304 even if a current or voltage is induced in the one or more lead wires.

As MM devices become more powerful, attempts to utilize electromagnetic shielding to protect leads from electromagnetic radiation, as have been used in the past, are unlikely to adequately protect against voltages and/or currents induced in lead wires, thereby causing injection current and/or voltage to propagate within IPG electronics 304 via the one or more lead wires 308 potentially damaging IPG electronics 304. As shown above, aspects of the present disclosure provide an automated technique for controlling electrical coupling and isolation of one or more lead wires 308 from IPG electronics 304 when IPG 324 is in the presence of electromagnetic radiation. The solution provided by IPG 324 addresses the problems associated with higher power MM scans by facilitating automated reconfiguration of IPG 324 between a therapeutic mode of operation and a MM-safe mode based on the presence of energetic electromagnetic radiation or lack thereof. In the therapeutic mode of operation, the switch(es) is placed into a conducive state to enable therapeutic operations via delivery of electrical stimulation via IPG electronics through one or more lead wires 308 to one or more electrodes of IMD 300. In the MRI-safe mode, the switch(es) is placed into the non-conductive state to electrically isolate IPG electronics 304 from the one or more lead wires 308, thereby preventing voltages and/or currents induced in one or more lead wires 308 from reaching IPG electronics 304. In this manner, heightened safety is provided without compromising operational integrity. It is to be understood that while primarily described with reference to electromagnetic radiation produced by a MM device, automatic triggering mechanisms for electrically isolating IPG electronics 304 from one or more lead wires 308 according to the present disclosure may be utilized to protect patients in any environment where electromagnetic radiation is present at sufficient power and/or with sufficient energy to induce currents and/or voltages in lead wires and are not limited to use with electromagnetic radiation generated from operation of MRI devices.

Figure 4:
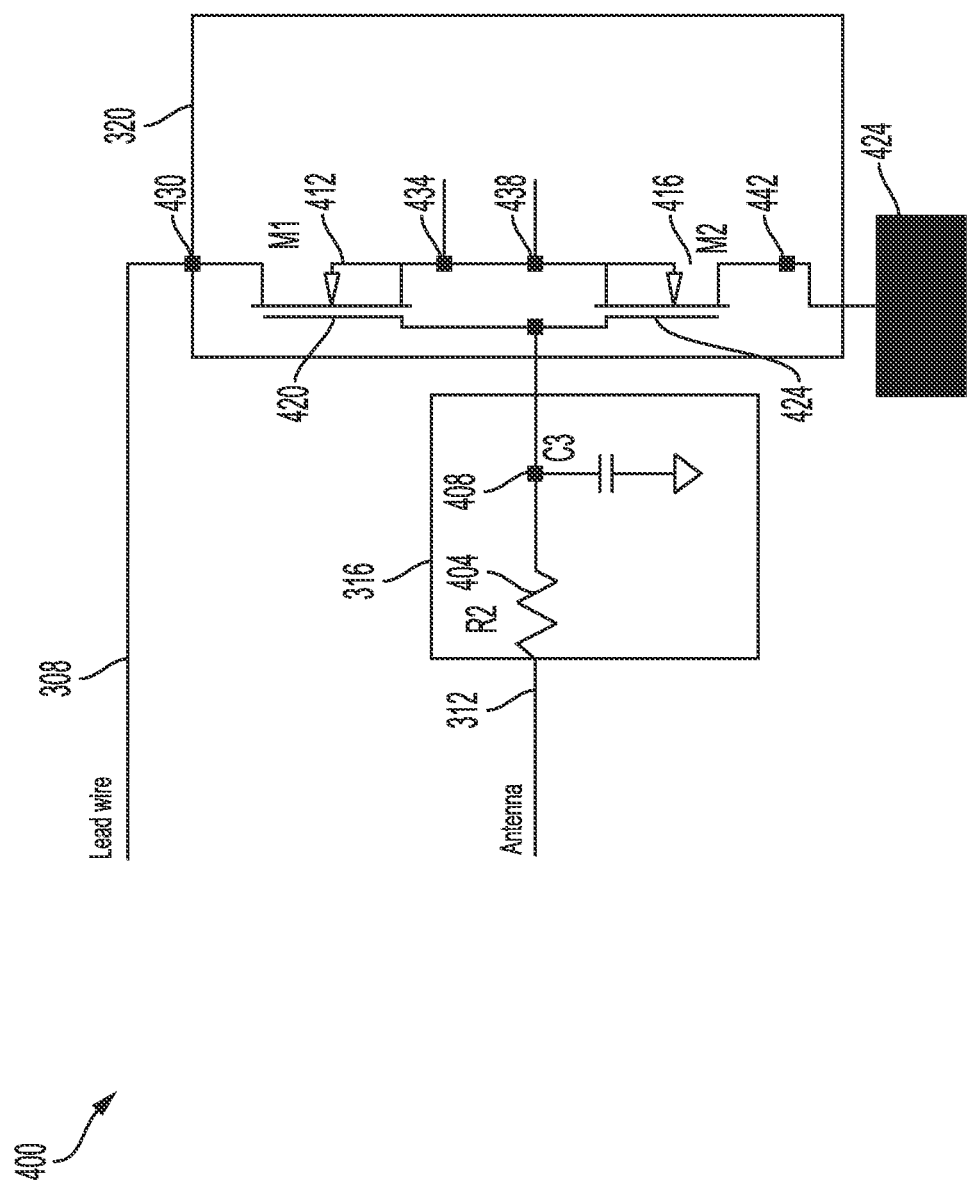
FIG. 4 shows a circuit diagram illustrating aspects of a MRI safe IMD according to embodiments of the present disclosure.

Referring to FIG. 4, a circuit diagram illustrating aspects of a MM-safe IMD 400 according to the present disclosure is shown as circuit 400. Circuit 400 includes switch 320 that is electrically coupled to lead wire 308 and to IPG electronics 304. Additionally, switch 320 is electrically coupled to antenna 312 possibly via filter 316.

In some aspects, switch 320 may be a solid state switch, such as one or more MOSFETs or one or more bipolar junction transistors (BJTs). In implementations in which switch 320 includes one or more MOSFETs, the control signal is provided to a gate of the MOSFET. For instance, in implementations in which switch 320 includes two back-to-back MOSFETs, such as first MOSFET 412 and second MOSFET 416 as depicted in FIG. 4, the control signal is simultaneously provided to first gate 420 of first MOSFET 412 and to second gate 424 of second MOSFET 416. Filter 316 may be configured to convert a voltage and/or current induced within antenna 312 by exposure to energetic electromagnetic radiation, such as by operation of a MRI device, into a smooth, approximately linear voltage corresponding to the control signal provided to the gates of the MOSFETs.

Filter 316 may be a RC filter having resistor 404 and capacitor 408 and configured to receive and process voltage or current signal from antenna 312. In implementations, first MOSFET 412 and second MOSFET 416 may be n-type depletion MOSFETs.

As depicted in FIG. 4, first source 430 of first MOSFET 412 is coupled to one or more lead wires 308. First drain 434 of first MOSFET 412 is coupled to second source 438 of second MOSFET 416. Second drain 442 of second MOSFET 416 is coupled to IPG electronics 304. During operation, such as while providing electrostimulation therapy, voltage and/or current is configured to propagate from IPG electronics 304 through second drain 442, second source 438, first drain 434, and first source 430 to lead wire 308 and ultimately to one or more electrodes (not depicted). However, when a patient is exposed to energetic electromagnetic radiation, such as while undergoing a MRI procedure, the energetic electromagnetic radiation excites antenna 312 and induces an excitation voltage or an excitation current in antenna 312. Filter 316 may smoothen the voltage signal to process the voltage signal into a control signal, which is provided to first gate 420 and second gate 424. The control signal applied to first gate 420 and second gate 424 causes first MOSFET 412 and second MOSFET 416 to become non-conductive. Accordingly, an injection current or voltage induced in one or more lead wires 308 by the energetic electromagnetic radiation cannot flow into IPG electronics 404, thereby protecting IPG electronics 404 from the injection current or voltage. When exposure of the IMD to the energetic electromagnetic radiation ceases, such as when the MRI procedure is complete, the excitation voltage or excitation current is no longer induced within antenna 312. Consequently, no control signal is applied to first gate 420 and to second gate 424, and first MOSFET 412 and second MOSFET 416 again automatically become conductive. In this manner, the IMD is reconfigured to provide electrostimulation therapy.

Although the switches described with reference to FIG. 4 are n-type depletion MOSFETs, in implementations, p-type MOSFETs may be used. In such implementations, an inverter may be positioned between filter 316 and the gates of the p-type MOSFETs so that a control signal provided to the gates of the p-type MOSFETs is a low voltage signal (e.g., corresponding to zero volts) to cause the p-type MOSFETs to enter a non-conductive state. In this way, IPG electronics 304 may be electrically isolated from one or more lead wires 308.

Figure 5:
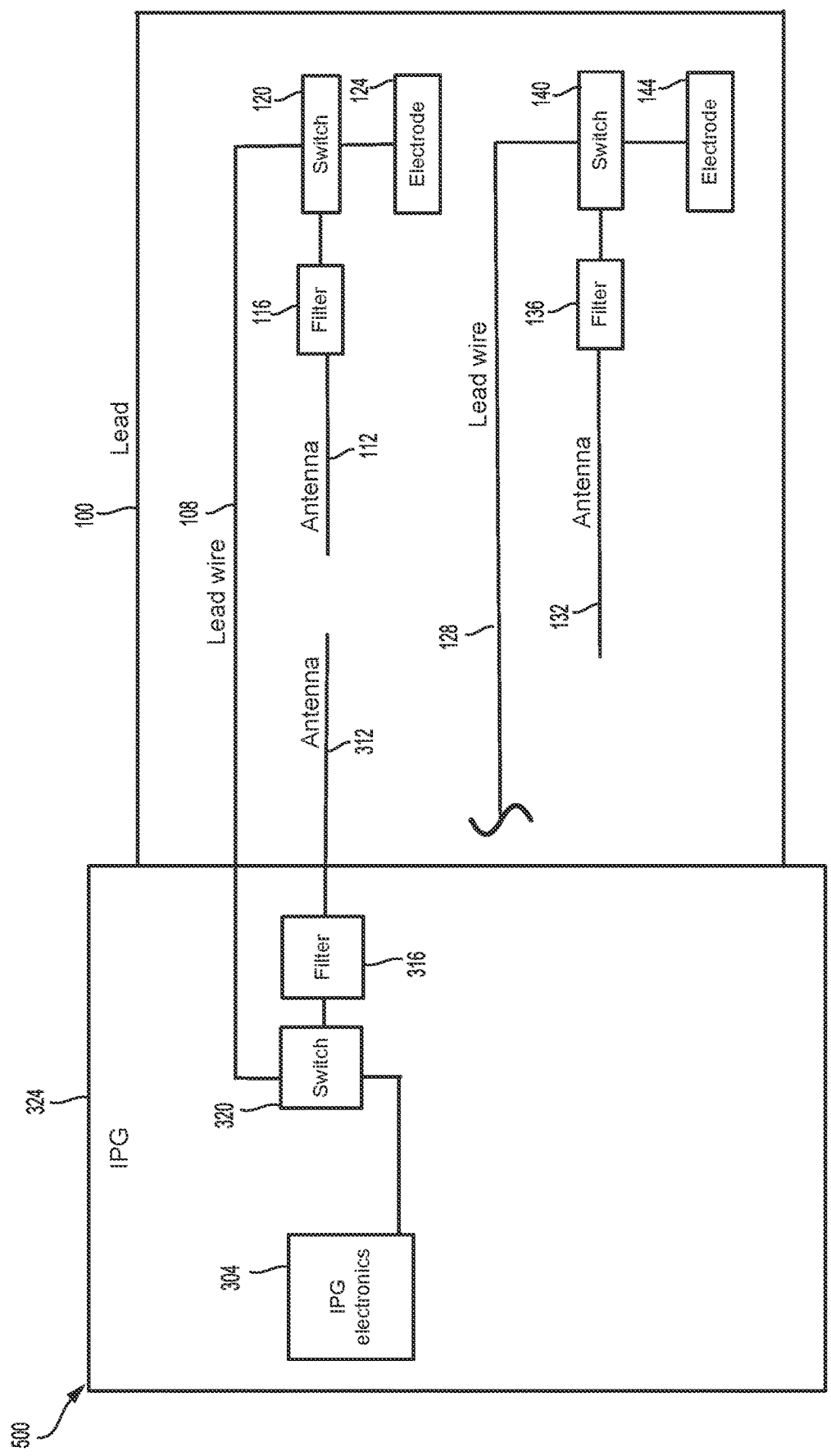
FIG. 5 shows a block diagram illustrating aspects of an IMD according to embodiments of the present disclosure.

Referring to FIG. 5, a block diagram illustrating aspects of an IMD according to the present disclosure is shown as IMD 500. IMD 500 includes lead 100 having lead wire 108, electrode 124, and antenna 112. Additionally, filter 116 may be positioned between antenna 112 and switch 120. As explained above with reference to FIG. 1. switch 120 is electrically coupled to antenna 112 and is configured to electrically isolate electrode 124 from lead wire 108 in response to a first control signal generated at antenna 112 by excitation of antenna 112 through exposure of IMD 500 to energetic electromagnetic radiation, such as is generated by operation of a MRI device. Electrical isolation of electrode 124 from lead wire 108 is configured to prevent an injection voltage and/or an injection current induced in lead 100 by the energetic electromagnetic radiation, such as generated by operation of the MM device, from entering electrode 124.

Additionally, lead 100 may include lead wire 128, switch 140, electrode 144, and antenna 132. As depicted in FIG. 5, switch 140 is electrically coupled to lead wire 128 and to electrode 144. Additionally, switch 140 is electrically coupled to antenna 132, possibly via filter 136. Antenna 132, filter 132, and switch are configured to operate similarly to antenna 112, filter 116, and switch 120, as explained above, and likewise are configured to electrically isolate lead wire 128 and electrode 144 when IMD 500 is exposed to energetic electromagnetic radiation. In embodiments, lead wire 128 may be electrically coupled to a switch (not depicted in FIG. 5) positioned within IPG 324 and the switch may be electrically coupled to IPG electronics 304 or other components of IPG 324. Moreover, the switch positioned within IPG 324 may be coupled to another antenna (not depicted) via another filter (not depicted). Alternatively or additionally, the switch positioned within IPG 324 may be coupled via another filter (not depicted) to antenna 132 or to an output of filter 316. Exemplary aspects of utilizing a single antenna to provide control signals to multiple switches are described in more detail with reference to FIG. 8. While lead 100 is depicted as having two lead wires, two switches, two filters, and two electrodes, lead 100 may include fewer or more lead wires, switches, filters and electrodes than as depicted in FIG. 5. As explained with reference to FIG. 1, electrodes 124, 144 may be any type of electrodes.

Additionally, IMD 500 includes IPG 324. IPG 324 includes IPG electronics 304 having electrical circuitry coupled to lead wire 108. Antenna 312, possibly coupled to filter 316, is configured to generate a control signal, which may be similar to the control signals generated by antennas 112, 132, in response to excitation of the antenna 312 by the energetic electromagnetic radiation generated, for example, by the MRI device. Moreover, IPG 324 includes switch 320 electrically coupled to antenna 312 and configured to electrically isolate electrical circuitry of IPG electronics 304 from lead wire 108. Electrical isolation of IPG electronics 304 from lead wire 108 is configured to prevent injection voltage and/or injection current induced in lead 104 by the energetic electromagnetic radiation generated, for example, by the MRI device from entering electrical circuitry of IPG electronics 304.

Filters 116, 136, 316 may be averaging filters, such as RC filters, configured to process one or more excitation voltages or excitation currents induced in antennas 112, 132, 312, respectively, to generate control signals that may be provided to switches 120, 140, 320, respectively, where the control signals control transition of switches 120, 140, 320 between the conductive and non-conductive states. Alternatively, filters 116, 136, 316 may be passive suppression filters configured to remove certain harmonics induced in antennas 112, 132, 312 by the energetic electromagnetic radiation (e.g., attenuate non-MRI frequencies, as described above). In some implementations, antennas 112, 132, 312 may be helically wrapped to increase a surface area of antennas 112, 132, 312 exposed to the energetic electromagnetic radiation. Additionally, antennas 112, 132, 312 may be fabricated from a material having equal, less than, or greater conductivity than a material from which lead wires 108, 128 are fabricated. Moreover, antennas 112, 312 may be fabricated from wire having a gage that is smaller than, equal to, or greater than a gage of lead wires 108. 128.

Energetic electromagnetic radiation, such as generated by operation of a MRI device, may induce a voltage and/or a current in antennas 112, 132, 312. The induced voltage and/or current may be provided to filters 116, 136, 316, respectively, which may process the induced voltage and/or current into one or more control signals. In response to receipt, at switch 120, of a control signal from antenna 112, switch 120 may transition to a non-conductive state, thereby electrically isolating electrode 124 from lead wire 108.

Similarly, in response to receipt, at switch 140, of a control signal from antenna 132, switch 140 may transition to a non-conductive state to electrically isolate switch 140 from electrode 144. Moreover, in response to receipt of a control signal from antenna 312 at switch 320, switch 320 may transition to a non-conductive state thereby electrically isolating IPG electronics 304 from lead wires 108, 128. When exposure of IMD 500 to the energetic electromagnetic radiation ceases, because, for instance, a MRI procedure being performed on the patient is complete, the control signals provided by antennas 112, 132, 312 may stop being generated. Switches 120, 140, 320 may be configured to detect that the control signals are no longer being received and, in response, switches 120, 140, and 320 may transition to a conductive state (e.g., switch 120 may electrically couple lead wire 108 to electrode 124, switch 140 may electrically couple lead wire 128 to electrode 144, and switch 320 may electrically couple IPG electronics 304 to lead wires 108, 128). Switches 120, 140 may be solid state switches as described with reference to FIG. 2, and switch 320 may be a solid state switch as described with reference to FIG. 4.

IMD 500 confers multiple advantages over the prior art. Antennas 112, 132 and switches 120,140 function to automatically place IMD 500 and its associated lead 100 into a MRI-safe mode in which electrodes 124, 144 are electrically isolated from lead wires 108, 128 in response to exposure of IMD 500 to energetic electromagnetic radiation. As MRI devices become more powerful, electromagnetic shielding techniques to attempt to shield leads (e.g., lead 100) from electromagnetic radiation, as used in the past, are unlikely to adequately protect against voltages and/or currents induced in lead wires, such as lead wires 108, 128, which may propagate to electrodes, such as electrodes 124, 144, thereby causing local tissue heating thus damaging tissue. Automated electrical isolation of lead wires, such as lead wires 108, 128, from electrodes, such as electrodes 124, 144, addresses the foregoing problem, while facilitating automated reconfiguration of IMD 500 into a conducive state when the energetic electromagnetic radiation is no longer present. Additionally, automatic electrical isolation of IPG electronics 304 from the lead wires 108, 128 may protect IPG electronics 304 from damage caused by injection voltage, thereby preventing damage to or potential failure of IPG electronics 304 when IMD 500 is in the presence of energetic electromagnetic radiation. As explained above, IPG electronics 304 may be automatically placed into the conductive state when IMD 500 is no longer in the presence of the energetic electromagnetic radiation, thereby allowing therapeutic operation of IMD 500 to resume when appropriate (e.g., when an MRI procedure is complete). In this manner, heightened safety is provided without compromising operational integrity. It is to be understood that while primarily described with reference to electromagnetic radiation produced by a MM device, automatic triggering mechanisms for electrically isolating electrodes 124, 144 and IPG electronics 304 from lead wires 108, 128 according to the present disclosure may be utilized to protect patients in any environment where electromagnetic radiation is present at sufficient power and/or with sufficient energy to induce currents or voltages in lead wires and are not limited to use with electromagnetic radiation generated from operation of MRI devices.

Figure 6:
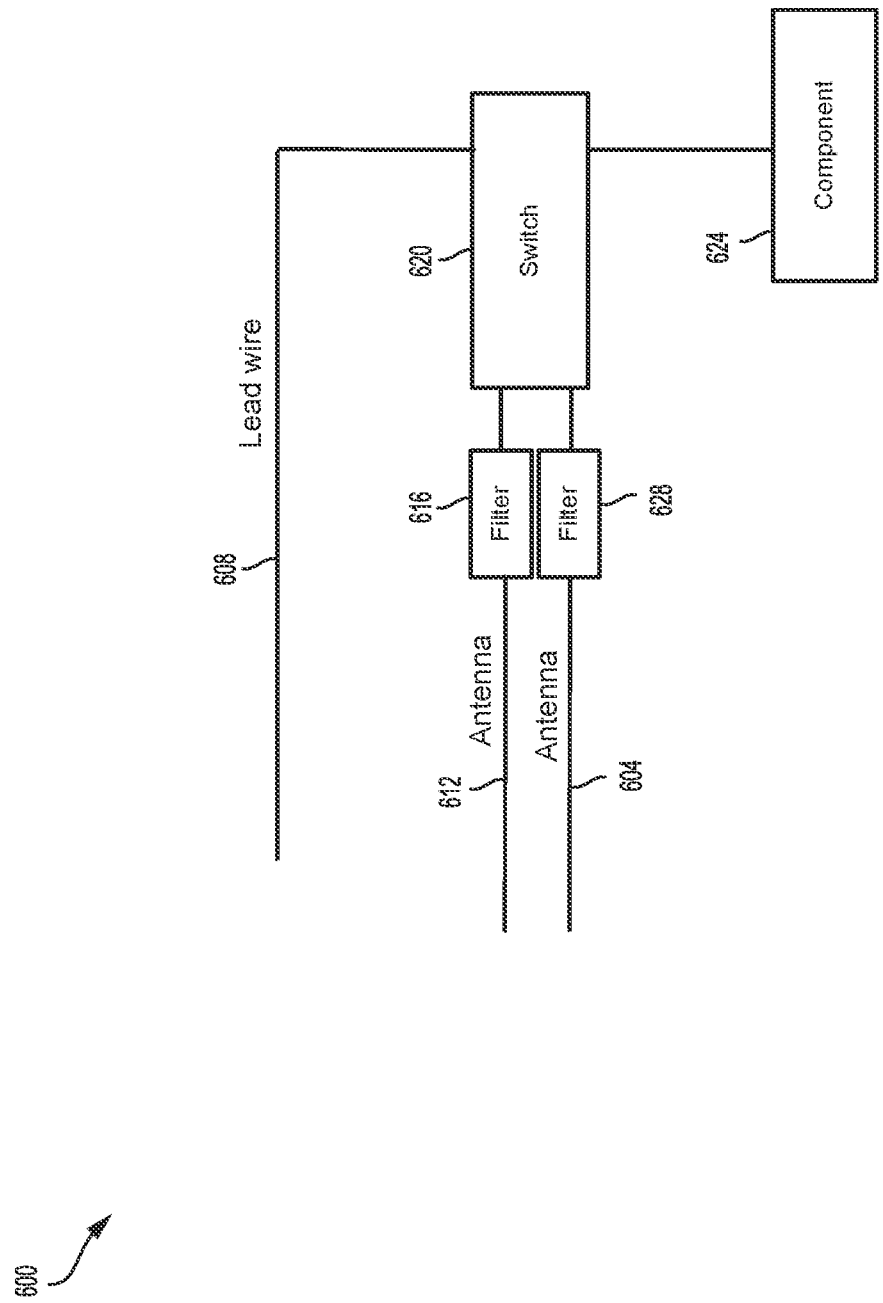
FIG. 6 shows a block diagram illustrating additional aspects of the IMD according to embodiments of the present disclosure.

Referring to FIG. 6, a block diagram illustrating additional aspects of an IMD according to the present disclosure is shown as IMD 600. In many circumstances, delivery of electrostimulation therapy is a critical application, such that, if the patient does not receive the electrostimulation therapy at appropriate times, the health and/or the life of the patient might be negatively affected. For instance, if IMD 600 is a pacemaker and if the IMD 600 ceases to function or functions improperly, the patient might die. Therefore, it is desirable to include back-up safety systems to prevent failure or improper operation of IMD 600.

As shown in FIG. 6, IMD 600 includes lead wire 608 and switch 620. Switch 620 is configurable to a conductive state and a non-conductive state. In the conductive state, switch 620 is configured to electrically couple lead wire 608 to component 624. In some implementations, component 624 may be an electrode, and the conductive state may permit electrical pulses to be provided from lead wire 108 to the electrode. In some implementations, component 624 may be IPG electronics, and the conductive state may permit electrical pulses to be provided from the IPG electronics to lead wire 108. In the non-conductive state and if component 624 is an electrode, switch 620 is configured to electrically isolate the electrode from lead wire 608. Additionally, in the non-conductive state and if component 624 is IPG electronics, switch 620 may be configured to electrically isolate the IPG electronics from lead wire 608 As illustrated in FIG. 6, switch 620 is electrically coupled to antenna 612 and to antenna 604. In some aspects, filter 616 and filter 628 may be provided to process control signals generated by antennas 612, 604, respectively. Antenna 604 may be provided as a failover or backup antenna to serve as a redundant antenna in case antenna 612, filter 616, or both do not function correctly, and antenna 612 may be provided as a failover or backup antenna to serve as a redundant antenna in case antenna 604, filter 628, or both do not function correctly.

To illustrate, if antenna 612, filter 616, or both are damaged, antenna 604 may be configured to provide a control signal to switch 620 in response to exposure of IMD 600 to energetic electromagnetic radiation. Thus, switch 620 can be configurable to the non-conductive state to electrically isolate component 624 from lead wire 608 even though antenna 612, filter 616, or both may not function properly to provide a control signal to switch 620. Similarly, if antenna 604, filter 628, or both are damaged, antenna 612 may be configured to provide a control signal to switch 620 in response to exposure of IMD 600 to energetic electromagnetic radiation. In this manner, switch 620 can be controlled to transition between the conductive state, in which component 624 is coupled to lead wire 608 for therapeutic operations, and the non-conductive state, in which component 624 is electrically isolated from lead wire 608, even though one of the antenna/filter pairs (e.g., antenna 604 and filter 628, or antenna 612 and filter 616) may not function properly to provide a control signal to switch 620. Therefore, failure of antenna 612 and/or filter 616 or the other of antenna 604 and/or filter 628 will not negatively affect the patient or operations of the 1 MB. Under normal operation antennas 604, 612 and filters 616, 628 may function properly and may provide redundant control signals to switch 620 to control transition of switch 620 between the conductive and non-conductive states, as described above.

Referring to FIG. 7, a block diagram illustrating aspects of a control antenna according to embodiments of the present disclosure is shown. As depicted in FIG. 7, antennas 112, 312 may be helically wrapped. Helically wrapping antennas 112, 312 may increase surface areas of antennas 112, 312 that are exposed to energetic electromagnetic radiation, such as generated by operation of a MM device.

By increasing a surface area of antenna 112, antenna 312, or both that is exposed to energetic electromagnetic radiation, a signal to noise ratio (SNR) of one or more voltage and/or current signals induced by the energetic electromagnetic radiation within antenna 112, antenna 312, or both may be higher than if antenna 112, antenna 312, or both are not helically wrapped. In this manner, a control signal provided to one or more switches, such as via one or more filters (e.g., RC filters, passive suppression filters, or other types of filters) may be more pronounced. In some implementations, antennas 112, 312 may be helically wrapped within lead 100. For example, antennas 112, 312 may be helically wrapped around one or more lead wires within lead 100 and/or around dielectric material that may surround the one or more lead wires. In other implementations, antennas 112, 312 may be helically wrapped around an outer surface of lead 100, which then may be covered with an insulating jacket. It is noted that the exemplary wrapping configurations described above have been provided for purposes of illustration, rather than by way of limitation and the other antenna wrapping configurations may be used in accordance with the concepts disclosed herein. Moreover, it is to be understood that the number of wraps for each antenna may be the same or different. For example, an antenna used to control a switch/electrode pair may be wrapped X times while an antenna used to control a switch/IPG electronics pair may be wrapped more than X times or less than X times.

Referring to FIG. 8, a block diagram illustrating additional aspects of an apparatus according to the present disclosure is shown as apparatus 800. In some implementations, apparatus 800 may be an IPG, a lead, or an 1 MB. Apparatus 800 includes antenna 812 electrically coupled, possibly via filter 816, to switches 820, 840. Switch 820, likewise, may be electrically coupled to lead wire 808, and switch 840 may be electrically coupled to lead wire 828. Component 824 may be coupled to lead wire 808 via switch 820. Similarly, component 844 may be coupled to lead wire 828 via switch 840. In response to excitation of antenna 812 by energetic electromagnetic radiation, such as generated by operation of a MRI device, antenna 812 may generate a voltage or current, possibly provided to filter 816 for processing. The voltage or current induced in antenna 812 may be provided as a control signal to switches 820, 840, causing switches 820, 840 to transition to a non-conductive state. Accordingly, switch 820 is configured to electrically isolate component 824 from lead wire 808, and switch 840 is configured to electrically isolate component 844 from lead wire 828 in response to the control signal provided by antenna 812 when apparatus 800 is exposed to energetic electromagnetic radiation. In some implementations, components 824, 844 may be components of an IPG, such as IPG electronics 304 of FIGS. 3 and 5 and/or other components of an 1 MB, such as IPG 324 of FIGS. 3 and 5. In other implementations, components 824, 844 may be electrodes, such as electrodes 124, 144 of FIGS. 1 and 5.

It is noted that while the description of FIG. 8 above illustrates using a single antenna to control multiple switches, each of which is configured to electrically couple components 824, 844 (e.g., electrodes or IPG electronics) to lead wires 808, 828, respectively, in some aspects a single, unitary antenna may be utilized to control electrical coupling and isolation of both IPG electronics and electrodes to lead wires. For example, in the exemplary arrangement shown in FIG. 8, assume that components 824, 844 are electrodes of a lead. A second filter (not shown in FIG. 8) may be placed at the end of antenna 812 opposite filter 816. The output of the second filter may be coupled to one or more switches (not shown in FIG. 8) associated with an IPG (not shown in FIG. 8) and that control electrical coupling and isolation of the IPG electronics to lead wires 808, 828 based on a control signal provided by antenna 812. Thus, when antenna 812 is exposed to energetic electromagnetic radiation, excitation of antenna 812 may be utilized to provide control signals at both ends of antenna 812, one control signal to control electrical isolation or coupling of IPG electronics from lead wires 808, 828 and another control signal to control electrical isolation or coupling of electrodes. It is noted that the embodiments of apparatus 800 described above may provide the benefit of ease of manufacture, since a single antenna, antenna 812, is electrically coupled to switches 820, 840 obviating the need to include a second antenna, as in some of the other embodiments disclosed herein. Additionally, even where an multiple antennas are utilized (e.g., utilizing a failover antenna to control both IPG-side and electrode-side electrical coupling/isolation, utilizing a first antenna to control IPG-side electrical coupling/isolation and a second antenna to control electrode-side electrical coupling/isolation, etc.), the ability to utilize a single antenna to control transition of multiple switches between the conductive state and the non-conductive state may provide some benefits, such as improved flexibility of the lead due to the reduced amount of wiring within the lead. Moreover, it is noted that while FIG. 8 shows antenna 812 as being configured to provide a control signal to two switches (e.g., switches 820, 840), it is to be understood that a single switch operating in accordance with the concepts described above with reference to FIG. 8 may be utilized to control more than two switches and may also be configured to provide control signals to switches on both the electrode and IPG side of a lead.

Figure 9:
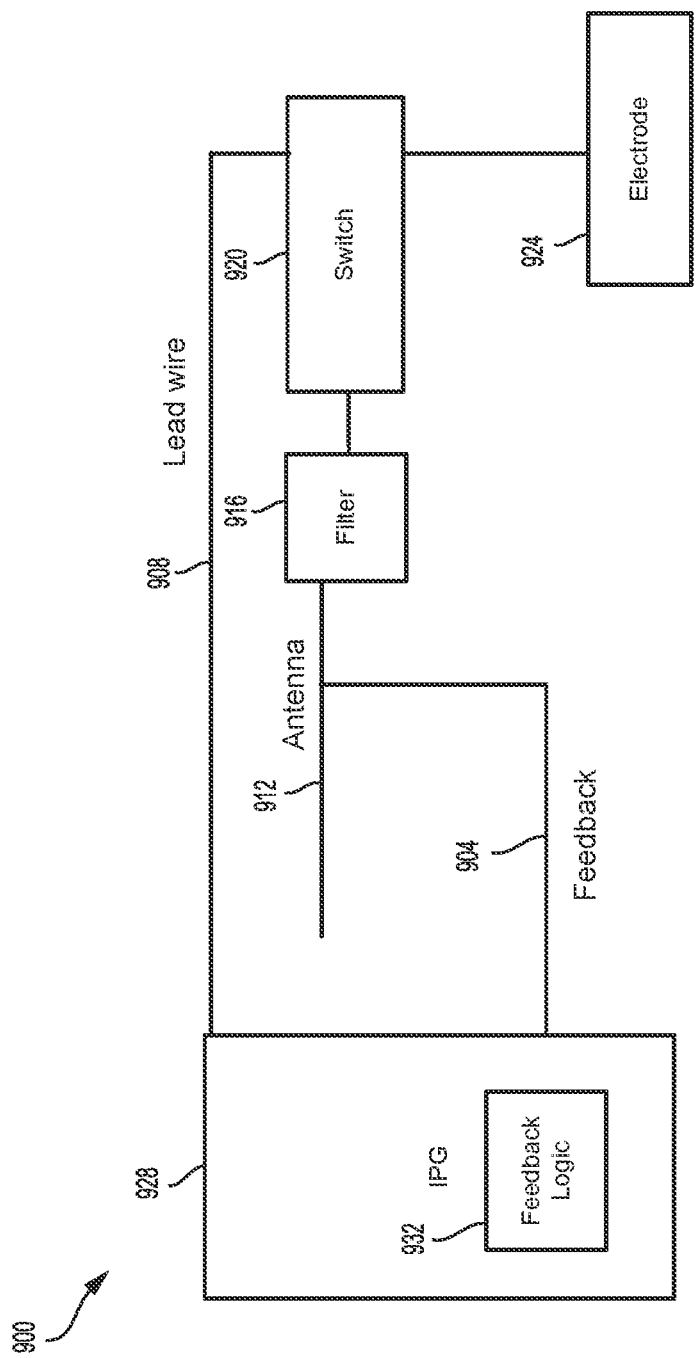
FIG. 9 is a block diagram illustrating aspects of a feedback control for an IMD according to embodiments of the present disclosure.

Referring to FIG. 9, a block diagram illustrating aspects of a feedback control for an IMD according to aspects of the disclosure is shown as an IMD 900. Since IMD 900 might be a mission-critical device, the failure of which could detrimentally affect the health of the patient in whom IMD 900 is implanted, it is generally advantageous for IMD 900 to be equipped with various safety features. Accordingly, depicted in FIG. 9 is feedback circuit 904, which may be a return electrical path from antenna 912 to IPG 928.

Feedback circuit 904, coupled to antenna 912 and to IPG 928, is configured to provide data from antenna 912 to IPG 928. IPG 928 may include feedback logic 932 (e.g., electrical circuitry, one or more processors, etc.) configured to utilize data received from feedback circuit 904 to assess electrical characteristics of antenna 912. An exemplary electrical characteristic of antenna 912 may include an impedance (e.g., an impedance measurement) of antenna 912. For example, filter 916 may be a RC filter having a resistor and a capacitor as depicted in FIG. 2. A capacitor of filter 916 may be non-conductive at certain low frequencies and may be conductive at certain higher frequencies. Therefore, if feedback circuit 904 provides an alternating current (AC) voltage at an appropriate frequency (e.g., one of the higher frequencies at which the capacitor is conductive), a current flow can be measured and an impedance of antenna 912 can be determined based on the current measurement. Alternatively or additionally, feedback logic 932 may include a time domain reflectometer (TDR) configured to characterize an electrical fault in antenna 912 based on signals received from feedback circuit 904. It is noted that the techniques described above for analyzing feedback received from feedback circuit 904 have been described for purposes of illustration, rather than by way of limitation. Accordingly, it is to be understood that other techniques and electrical characteristics may be utilized by feedback logic 932 to evaluate feedback or signals received via feedback circuit 904 and the status of antenna 912.

Feedback logic 932 of IPG 928 may measure (e.g., periodically, continuously, or in response to a command from a clinician or patient) the electrical characteristic of antenna 912 via feedback circuit 904. Upon obtaining the measurement, IPG 928 may compare the measured characteristic (e.g., impedance) to a threshold to determine an operating state of antenna 912. For example, if a break in the wire of antenna 912 occurs, the measured characteristic may change. When the measured characteristic satisfies the threshold, feedback logic 932 may determine that antenna 912 is operating in a normal state (i.e., no damage to antenna 912). When the measured characteristic does not satisfy the threshold, feedback logic 932 may determine that antenna 912 is operating in a damaged state.

As another example, feedback logic 932 may be configured to compare an impedance measurement of antenna 912 obtained via feedback circuit 904 against a threshold impedance value stored in a memory, such as a memory of IMD 900. In response to determining that the impedance measurement exceeds the threshold impedance value, feedback logic 932 may be configured to activate a battery (not depicted) of IPG 928 to provide a bias voltage to switch 920 to cause switch 920 to enter a non-conductive state, thereby electrically isolating electrode 924 from lead wire 908. Thus, an antenna failure, such as failure of antenna 912, can automatically trigger IMD 900 to enter into a MM safe mode. Additionally or alternatively, an antenna failure may cause IMD 900 to generate an alert, provided to the patient, a clinician, or both, via a patient programmer device, a clinician programmer device, or both. Moreover, when multiple antennas are used, such as with reference to any of FIGS. 1, 5, and 6, a feedback circuit may be provided for each antenna to detect an operation state of each antenna as described above.

Figure 10:
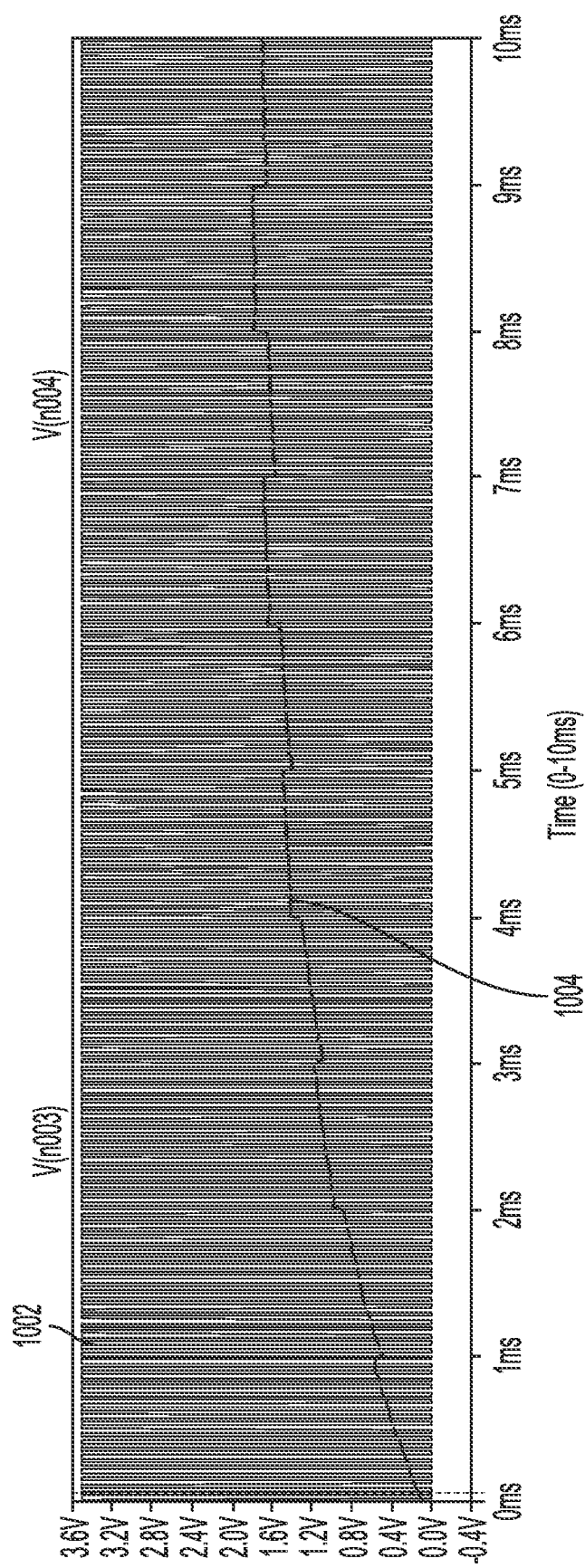
FIG. 10 is a graph depicting operational effects of a filter according to embodiments of the present disclosure.

As explained with reference to FIGS. 1-9, a filter, such as a RC filter, positioned between an antenna and a switch, may be configured to process a voltage signal induced in the antenna by energetic electromagnetic radiation, such as by a MRI device, so that a control signal provided to the switch by the filter is roughly linear and continuous. Referring to FIG. 10, a graph depicting the effects of the operation of a filter on a control signal in accordance with the present disclosure is shown. In particular, the graph of FIG. 10 shows the impact of using a filter to process voltage signal 1002 induced by an antenna in the presence of electromagnetic radiation to produce control signal 1004.

Voltage signal 1002 may be induced in an antenna (e.g., any of the antennas described an illustrated with reference to FIGS. 1-9) by energetic electromagnetic radiation, such as generated by a MRI device. At least due to rapid oscillations in a magnetic field generated by the MM device, an amplitude of voltage signal 1002 may fluctuate rapidly with respect to time as depicted in FIG. 10. A filter, such as any of the filters described and illustrated with reference to FIGS. 1-9, positioned between the antenna and the switch may process rapidly fluctuating voltage signal 1002 to produce, as an output, the continuous and relatively linear control signal 1004 (also a voltage signal). The filter may further be configured to provide control signal 1004 to the switch (e.g., a gate of a MOSFET) to cause the switch to enter a non-conductive state. As explained above with reference to FIGS. 1-9, other averaging filters or other types of filters may also be used to produce a continuous and smooth control signal.

Figure 11:
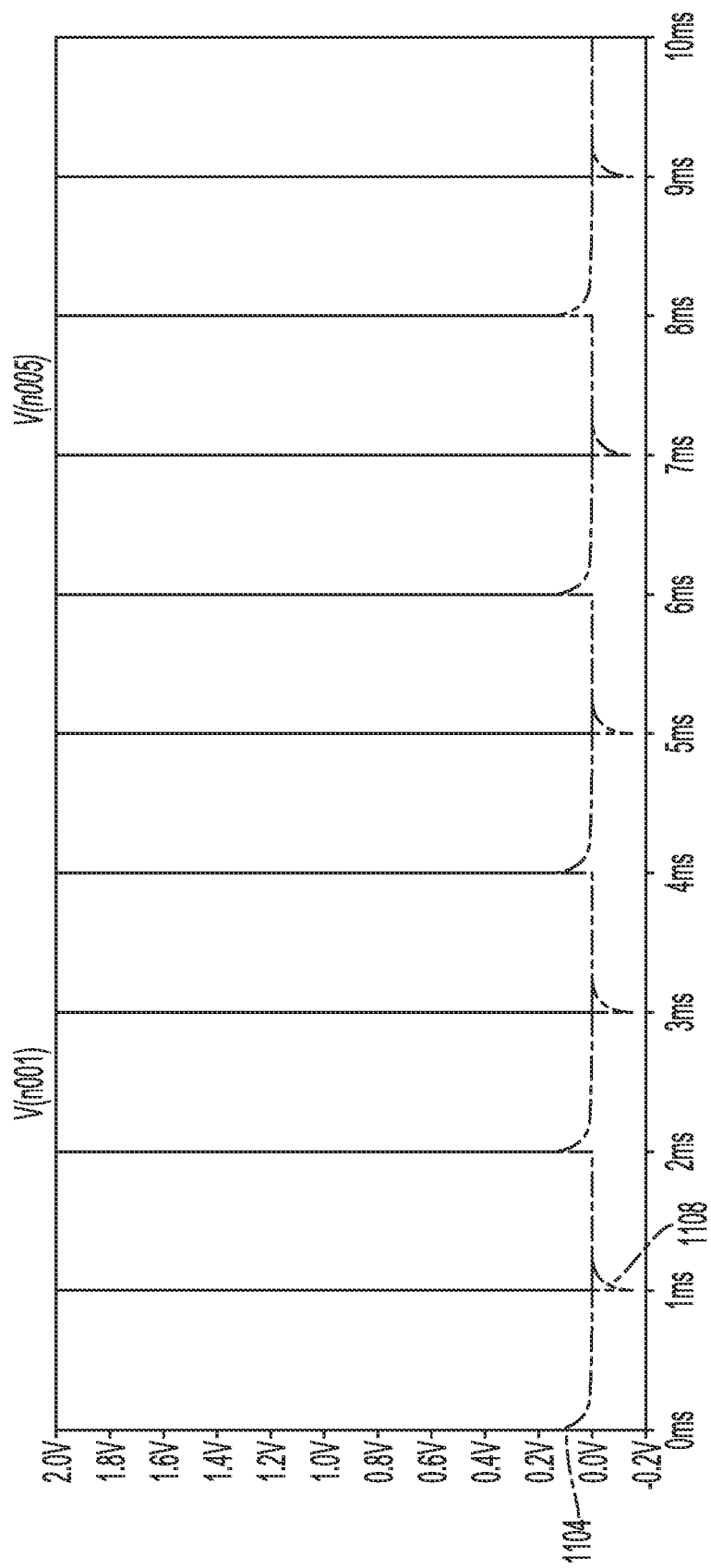
FIG. 11 is a graph illustrating voltage versus time for an IMD according to embodiments of the present disclosure.

Referring to FIG. 11, a graph illustrating voltage versus time for an IMD according to embodiments of the present disclosure is shown. While putting a switch in a non-conductive state electrically isolates IPG electronics and/or electrodes from one or more lead wires of a lead, some voltage induced in one or more lead wires by energetic electromagnetic radiation, such as induced by operation of a MRI device, may, nevertheless, leak into the IPG electronics, the electrode, or both. For example, as depicted in FIG. 11, first injection voltage 1104 of less than 0.2 V may leak into an electrically isolated electrode between 0 ms and 1 ms and second injection voltage 1108 of less than −0.2 V may leak into the electrically isolated electrode between 1 ms and 2 ms while an IMD is exposed to energetic electromagnetic radiation, such as when a patient undergoes a MRI procedure. It has been empirically determined that exposure of cells, such as nerve cells, to voltages of the magnitude depicted in FIG. 11 for the timeframes shown in FIG. 11 is insufficient to cause cellular damage.

Figure 12:
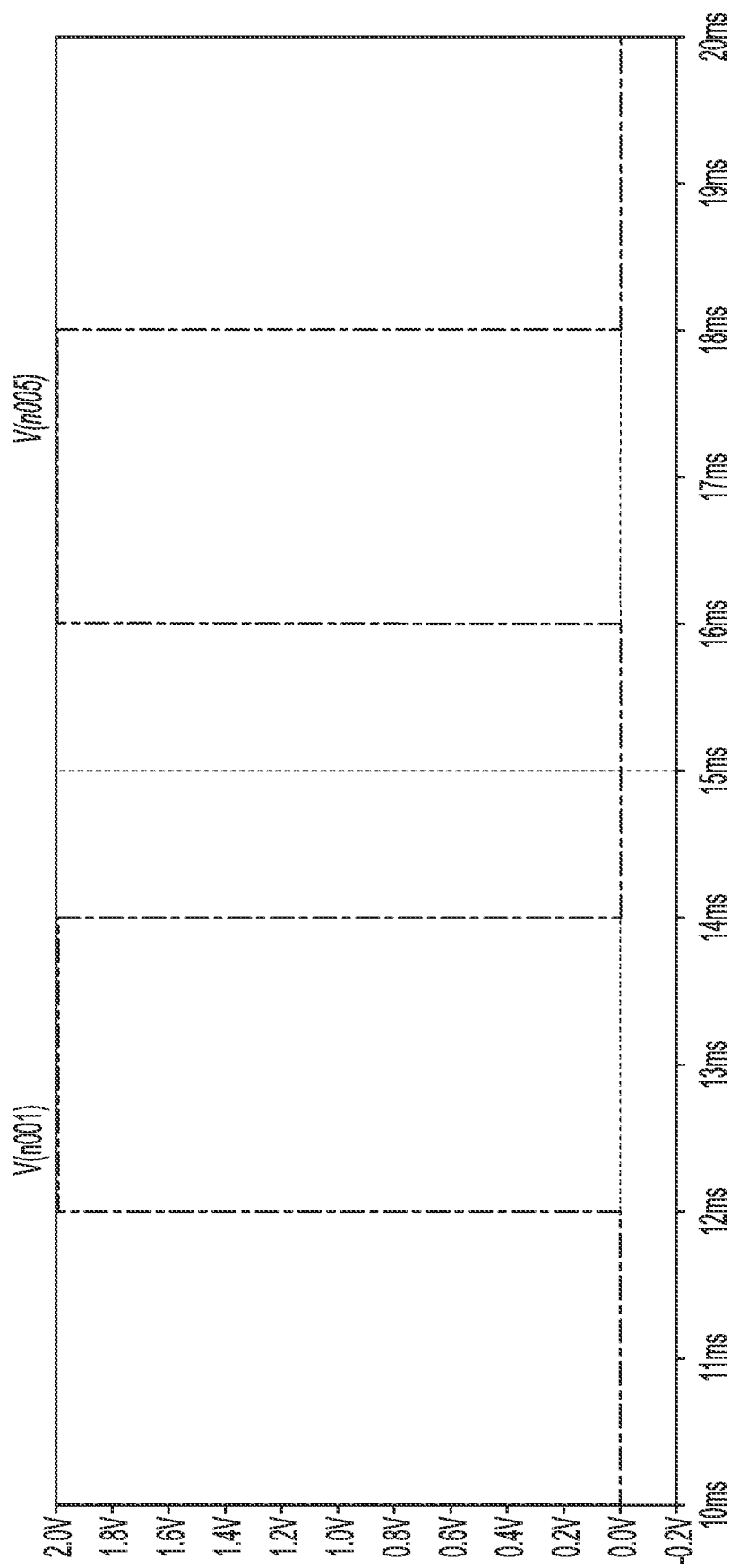
FIG. 12 is a graph showing periodic voltages provided by one or more electrodes of an IMD to a patient during a therapy session according to embodiments of the present disclosure.

Referring to FIG. 12, a graph showing periodic voltages provided by one or more electrodes of an IMD to a patient during a therapy session is shown. As explained with reference to FIGS. 1-9, in the absence of energetic electromagnetic radiation, such as when a MRI procedure is complete, and one or more switches reenter a conductive state, a voltage (e.g., an electrical pulse generated by an IPG) delivered by one or more electrodes of the IMD to tissue surrounding the one or more electrodes returns to a voltage level commensurate with a therapy session. For example, as depicted in FIG. 12, one or more electrodes of an IMD provides a periodic voltage of 2.0 volts (V) to tissue surrounding the one or more electrodes in the absence of energetic electromagnetic radiation. Therefore, the antenna-filter-switch architecture depicted in FIGS. 1-9 is configured to maintain a quality of therapy provided by the IMD while simultaneously providing the ability to protect electrodes and/or electronics from injection voltage induced in one or more lead wires of a lead by energetic electromagnetic radiation.

Figure 13:
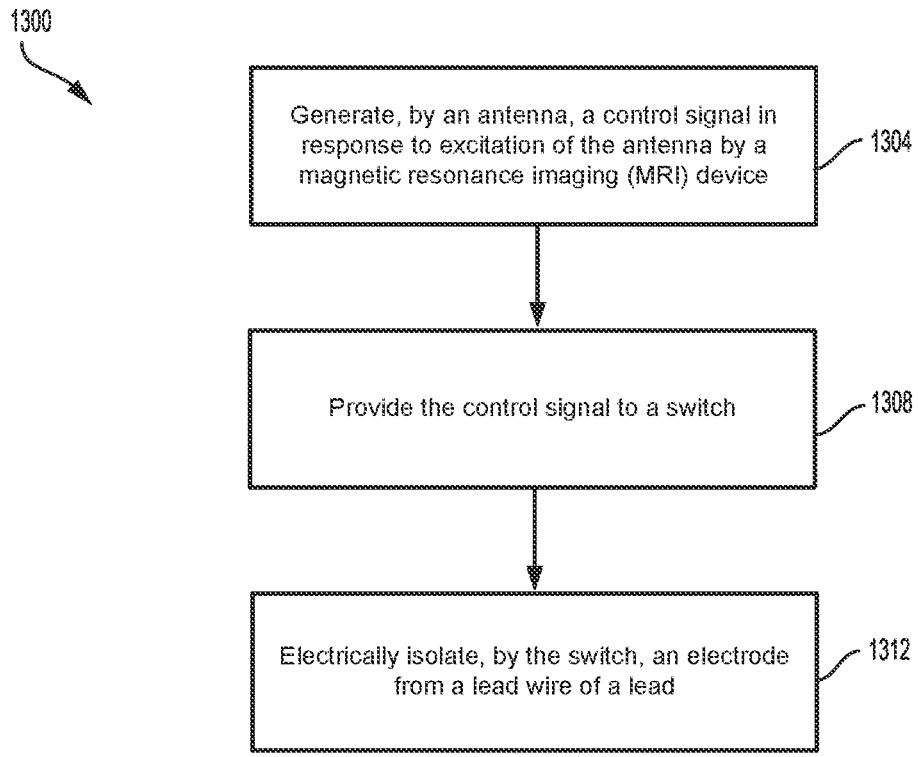
FIG. 13 is a flow chart illustrating aspects of a method for preventing transmission of induced voltages to one or more electrodes of an IMD according to embodiments of the present disclosure.

Referring to FIG. 13, a flow chart illustrating aspects of a method for preventing transmission of induced voltages to one or more electrodes of an IMD according to the present disclosure is shown as a method 1300. At block 1304, method 1300 includes generating, by an antenna, a control signal. As described above, the control signal may be generated by the antenna in response to excitation of the antenna by energetic electromagnetic radiation, such as emitted by a MM device. For example, an antenna, such as the antennas described with reference to FIGS. 1, 2, 5, 6, 8, and 9 may generate a voltage signal (e.g., voltage signal 1002 as depicted in FIG. 10) in response to excitation by energetic electromagnetic radiation. As described above, a filter, such a RC filter or other averaging filter, may be configured to process the voltage signal induced by the antenna into a continuous and roughly linear control signal, such as control signal 1004 as depicted in FIG. 10.

At block 1308, method 1300 includes providing the control signal to a switch. For example, the antenna and/or filter may be configured to provide the control signal to one or more switches as described with reference to FIGS. 1, 2, 5, 6, 8, and 9. As explained with reference to FIG. 2, the one or more switches may be solid state switches, such as fabricated from MOSFETs and the control signal may be provided to gates of MOSFETs.

At block 1312, method 1300 includes electrically isolating, by the one or more switches, one or more electrodes from one or more lead wires of a lead. As described above, the one or more switches may transition between a non-conductive and conductive state in response to the control signal, as explained more fully with reference to FIG. 2. In this manner, an injection voltage (or an injection current) induced in the one or more lead wires by the energetic electromagnetic radiation does not propagate into the one or more electrodes electrically coupled to the one or more lead wires via the one or more switches. Accordingly, a patient, in whose body an IMD is placed, is protected from an injection voltage and/or an injection current induced in the one or more lead wires by energetic electromagnetic radiation, such as produced by a MRI device. As explained with reference to FIGS. 1, 2, 5, 6, 8, and 9, when the energetic electromagnetic radiation is no longer present, because, for instance, a MRI procedure is complete, the antenna no longer generates a control signal. Hence, the control signal is no longer provided to the one or more switches, and the one or more switches transition to the conductive state in which the lead wire(s) are in electrical communication with the electrode(s) via the switch(es). In this manner, a voltage generated by an IPG of the IMD is able to propagate through one or more lead wires to the one or more electrodes, thereby delivering therapeutic electric pulses to the patient.

Figure 14:
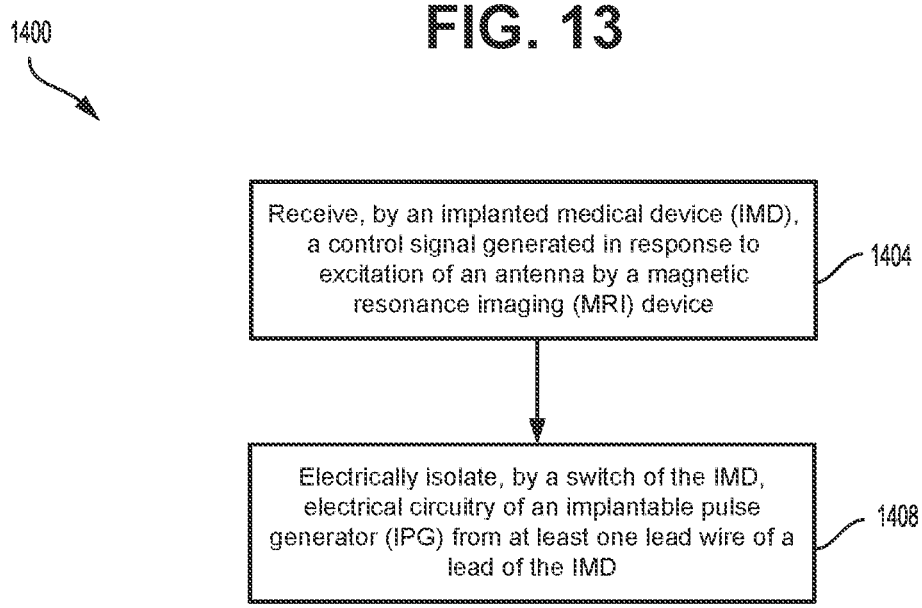
FIG. 14 is a flow chart illustrating aspects of a process to protect electrical circuitry of an IPG of an IMD from an injection voltage induced in one or more lead wires of a lead by energetic electromagnetic radiation according to embodiments of the present disclosure.

Referring to FIG. 14, a flow chart illustrating aspects of a method for preventing transmission of induced voltages and/or currents into electrical circuitry of an IPG according to the present disclosure is shown as method 1400. At block 1404, an IMD receives a control signal generated in response to excitation of an antenna by energetic electromagnetic radiation, such as produced by a MRI device. For example, a switch of an IPG of the IMD may receive the control signal from one or more antennas via a filter, such as RC filter or other averaging filter. In implementations, the switch may be a solid state switch, such as formed from one or more metal oxide semiconductor field effect transistors (MOSFETs) or bipolar junction transistors (BJTs).

At 1408, electrical circuitry of the IPG is electrically isolated by the switch of the IMD. In particular, receipt, at the switch, of the control signal causes the switch to be configurable to a non-conductive state. For instance, in implementations in which the switch includes two back-to-back MOSFETs, as described with reference to FIG. 4, the control signal is provided to a gate of each MOSFET of the back-to-back MOSFETs. The voltage, corresponding to the control signal, received at the gates of the MOSFETs causes the MOSFETs to become non-conductive. Accordingly, injection voltage (or injection current) induced by energetic electromagnetic radiation in one or more lead wires of a lead of the IMD cannot propagate from the one or more lead wires through the switch into the electrical circuitry of the IPG. When the IMD is no longer exposed to the energetic electromagnetic radiation because, for example, a MRI procedure being undergone by a patient in whom the IMD is implanted is complete, the control signal is no longer provided to the gates of the MOSFETs; consequently, the MOSFETs return to a conductive state. Accordingly, electrical pulses generated by the IPG during a therapy session can travel from the IPG through the switch into the one or more lead wires and thereafter to one or more electrodes for delivery of electrical stimulation therapy to the patient.

As shown above, embodiments of the present disclosure utilize antennas and switches to automatically place IMDs or specific components of the IMDs (e.g., an IPG or electrodes of a lead) into a MM-safe mode in which IPG electronics and/or electrodes are electrically isolated from lead wire(s). The ability to automatically trigger configuration of an IMD to a MM-safe mode represents an improvement over previous MRI-safe mode activation mechanisms that required manual activation by a clinician or a patient. Moreover, it is noted that the automated mechanisms for triggering MM-safe mode disclosed herein may be used in conjunction with manual activation mechanisms. For example, the automated triggering mechanisms of embodiments may provide a fail-safe mechanism for placing IMDs into a MM-safe mode in the event that an operator (e.g., a clinician or patient) forgets to trigger the manual activation mechanism prior to exposing an IMD to energetic electromagnetic radiation. It is to be understood that while primarily described with reference to electromagnetic radiation produced by a MRI device, automatic triggering mechanisms for electrically isolating IPG electronics and/or electrodes from lead wires according to the present disclosure may be utilized to protect IMDs and patients in any environment where electromagnetic radiation is present at sufficient power and/or with sufficient energy to induce currents or voltages in lead wires and are not limited to use with electromagnetic radiation generated from operation of MRI devices.

It should be understood that the various embodiments shown in FIGS. 1-9 may be utilized in combination with one another. For example, any of the embodiments shown in FIGS. 1-6, 8, and 9 may utilize wrapped antennas as described with reference to FIG. 7. As another example, any of the embodiments of FIGS. 1-5 and 7-9 may utilize failover antennas of FIG. 6. Also, the feedback circuits of FIG. 9 may be utilized with any of the embodiments illustrated in FIGS. 1-8; and antennas providing control over multiple switches, as described with reference to FIG. 8, may be utilized to control coupling/isolation of IPG electronics, electrodes, or both, such as to provide control of coupling/isolation of IPG electronics 304 of FIG. 5 to lead wire 128 of FIG. 5. Additionally, it is noted that while switches for controlling electrical coupling/isolation of IPG electronics are primarily described with reference the switches being incorporated into the IPG, such switches may be disposed external to the IPG or suitable location where injection currents may be prevented from entering the IPG or otherwise mitigating the impact of any injection currents that do enter the IPG. For example, the switch may be disposed in the lead proximate an end of the lead that is coupled to terminals of the IMD or IPG, between terminals used to couple the lead to the IPG or IMD and the IPG electronics, or another location. Additionally, in some implementations, rather than being disposed in the lead, antennas utilized to control electrical isolation of the IPG electronics may be wrapped about or otherwise disposed within the IPG itself. Other exemplary combinations and modifications of the exemplary embodiments disclosed herein will be apparent to those of skill in the art.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

What is claimed is:

1. An apparatus comprising:
    a lead comprising:
        a first lead wire;
        a second lead wire;
        a first electrode; and
        a second electrode;
    a first antenna configured to generate a first control signal in response to excitation of the first antenna by a magnetic resonance imaging (MRI) device;
    a first switch electrically coupled to the first antenna and configured to electrically isolate the first electrode from the first lead wire in response to the first control signal; and
    a second switch electrically coupled to the first antenna and configured to electrically isolate the second electrode from the second lead wire in response to the first control signal.

2. The apparatus of claim 1, further comprising a first filter positioned between the first antenna and the first switch, wherein the first filter is a resistor capacitor (RC) filter configured to linearize a voltage corresponding to the first control signal.

3. The apparatus of claim 1, wherein the first switch is a solid state switch.

4. The apparatus of claim 1, wherein the first switch comprises a first metal oxide semiconductor field effect transistor (MOSFET) and a second MOSFET, wherein a drain of the first MOSFET is coupled to a source of the second MOSFET.

5. The apparatus of claim 4, further comprising:
    a first diode coupled to the first MOSFET; and
    a second diode coupled to the first diode and to the second MOSFET, wherein the first diode has an opposite polarity to the first diode.

6. The apparatus of claim 4, wherein the first control signal is provided to a first gate of the first MOSFET and to a second gate of the second MOSFET, and wherein, in response to receipt of the first control signal, the first MOSFET and the second MOSFET are configurable to a non-conductive state.

7. The apparatus of claim 1, wherein the first electrode is a bipolar electrode configured to provide biphasic pulses to tissue surrounding the first electrode, and wherein the first antenna is wrapped at least partially around a circumference of the lead and the first lead wire.

8. The apparatus of claim 1, further comprising a failover antenna coupled to the first switch and configured to generate and provide a redundant control signal to the first switch in response to excitation of the failover antenna by the MRI device.

9. The apparatus of claim 1, wherein the lead further comprises a plurality of lead wires and a plurality of electrodes, wherein the apparatus further comprises a plurality of switches and a plurality of antennas, wherein each switch of the plurality of switches is electrically coupled to an antenna of the plurality of antennas, and wherein each switch of the plurality of switches is configured to electrically isolate an electrode of the plurality of electrodes from a lead wire of the plurality of lead wires in response to a control signal generated at the antenna.

10. An implanted medical device (IMD) comprising:
    a lead, the lead comprising:
        at least one lead wire; and
        an antenna configured to generate a control signal in response to excitation of the antenna by a magnetic resonance imaging (MRI) device; and
    an implantable pulse generator (IPG) having electrical circuitry coupled to the lead, wherein the IPG comprises a switch electrically coupled to the antenna of the lead and configured to electrically isolate the electrical circuitry of the IPG from the at least one lead wire in response to the control signal, and wherein the IPG is configured to:
        measure an electrical characteristic of the antenna; and
        determine whether to active an MRI mode of the IPG based on the electrical characteristic.

11. The IMD of claim 10, wherein electrically isolating the electrical circuitry of the IPG from the at least one lead wire is configured to protect the electrical circuitry of the IPG from an injection voltage induced by the MRI.

12. The IMD of claim 10, wherein the switch comprises a solid state switch, wherein the solid state switch comprises at least one metal oxide semiconductor field effect transistor (MOSFET), and wherein the control signal is provided to a gate of the at least one MOSFET.

13. The IMD of claim 12, wherein the switch comprises a second MOSFET coupled to the at least one MOSFET, and wherein the control signal is simultaneously provided to the gate of the at least one MOSFET and to a second gate of the second MOSFET.

14. The IMD of claim 10, wherein the electrical characteristic of the antenna includes an impedance of the antenna, and wherein, in response to a determination, at the IPG, that the impedance is above a threshold value, the IPG is configured to apply a bias voltage at the switch to electrically isolate the electrical circuitry of the IPG from the at least one lead wire.

15. An implantable medical device (IMD) comprising:
    a lead comprising:
        a first lead wire;
        an electrode;
        a first antenna configured to generate a first control signal in response to excitation of the first antenna by a magnetic resonance imaging (MRI) device;
        a first switch electrically coupled to the first antenna and configured to electrically isolate the electrode from the first lead wire in response to the first control signal, wherein electrical isolation of the electrode from the first lead wire is configured to prevent a first injection voltage induced in the lead by the MRI device from entering the electrode; and
        a first resistor-capacitor (RC) filter positioned between the first antenna and the first switch, wherein the first RC filter is configured to linearize a voltage corresponding to the first control signal; and
    an implantable pulse generator (IPG) comprising:
        IPG electronics having electrical circuitry coupled to the first lead wire, wherein a second antenna is further configured to generate a second control signal in response to excitation of the second antenna by the magnetic resonance imaging (MRI) device; and
        a second switch electrically coupled to the second antenna and configured to electrically isolate the electrical circuitry of the IPG electronics from the first lead wire in response to the second control signal, wherein electrical isolation of the IPG electronics from the first lead wire is configured to prevent injection voltage induced in the lead by the MRI device from entering the electrical circuitry of the IPG electronics.

16. The IMD of claim 15, wherein the first antenna is independent of the second antenna, and wherein the first antenna and the second antenna are helically wrapped around a circumference of the lead, and wherein the second antenna is positioned within the lead.

17. The IMD of claim 15, wherein a second RC filter is positioned between the second antenna and the second switch, and wherein the first antenna and the second antenna are fabricated from a material having a greater conductivity than the first lead wire.

18. The IMD of claim 15, wherein the first antenna and the second antenna include a return path to the IPG, wherein the IPG is configured to measure electrical characteristics of the first antenna and the second antenna, and wherein an electrical characteristic of the electrical characteristics includes a first impedance of the first antenna and a second impedance of the second antenna.

\* \* \* \* \*

UNITED STATES PATENT AND TRADEMARK OFFICE
CERTIFICATE OF CORRECTION

PATENT NO. : 11,779,757 B2
APPLICATION NO. : 17/382294
DATED : October 10, 2023
INVENTOR(S) : Matthew Lopez It is certified that error appears in the above-identified patent and that said Letters Patent is hereby corrected as shown below:

In the Specification

At Column 1, Line number 10, delete "(MM) devices" and replace with --(MRI) devices--.
At Column 2, Line number 7, delete "Mill device" and replace with --MRI device--.
At Column 2, Line number 52, delete "MM devices" and replace with --MRI devices--.
At Column 3, Line number 2, delete "MM safe mode" and replace with --MRI safe mode--.
At Column 3, Line number 10, delete "MM safe mode" and replace with --MRI safe mode--.
At Column 3, Line number 21, delete "MM scan" and replace with --MRI scan--.
At Column 3, Line number 24, delete "MM devices" and replace with --MRI devices--.
At Column 3, Line number 52, delete "MM device" and replace with --MRI device--.
At Column 4, Line number 39, delete "MM device" and replace with --MRI device--.
At Column 4, Line number 46, delete "MM device" and replace with --MRI device--.
At Column 6, starting at Line number 27, delete "MM compatible" and replace with --MRI compatible--.
At Column 7, Line number 52, delete "MM procedure" and replace with --MRI procedure--.
At Column 7, Line number 53, delete "MM procedure" and replace with --MRI procedure--.
At Column 8, Line number 28, delete "MM device" and replace with --MRI device--.
At Column 9, Line number 29, delete "MM devices" and replace with --MRI devices--.
At Column 9, Line number 42, delete "MM-safe mode" and replace with --MRI-safe mode--.
At Column 9, Line number 47, delete "MM-safe mode" and replace with --MRI-safe mode--.
At Column 9, Line number 54, delete "MM device" and replace with --MRI device--.
At Column 9, Line number 63, delete "MM-safe lead" and replace with --MRI-safe lead--.
At Column 11, starting at Line number 59, delete "MM procedure" and replace with --MRI procedure--.
At Column 12, Line number 10, delete "MM devices" and replace with --MRI devices--.
At Column 12, Line number 23, delete "MM scans" and replace with --MRI scans--.
At Column 12, Line number 25, delete "MM-safe mode" and replace with --MRI-safe mode--.
At Column 12, Line number 39, delete "MM device" and replace with --MRI device--.
At Column 12, Line number 48, delete "MM-safe IMD" and replace with --MRI-safe IMD--.

Signed and Sealed this
Fourteenth Day of November, 2023

*Katherine Kelly Vidal*
Katherine Kelly Vidal
*Director of the United States Patent and Trademark Office*

CERTIFICATE OF CORRECTION (continued)
U.S. Pat. No. 11,779,757 B2

At Column 13, Line number 63, delete "MM device" and replace with --MRI device--.
At Column 15, Line number 55, delete "MM device" and replace with --MRI device--.
At Column 16, Line number 54, delete "1 MB" and replace with --IMD--.
At Column 16, Line number 65, delete "MM device" and replace with --MRI device--.
At Column 17, Line number 29, delete "1 MB" and replace with --IMD--.
At Column 17, Line number 51, delete "1 MB" and replace with --IMD--.
At Column 19, Line number 29, delete "MM safe mode" and replace with --MRI safe mode--.
At Column 19, Line number 54, delete "MM device" and replace with --MRI device--.
At Column 20, Line number 48, delete "MM device" and replace with --MRI device--.
At Column 21, Line number 64, delete "MM-safe mode" and replace with --MRI-safe mode--.
At Column 21, Line number 67, delete "MM-safe mode" and replace with --MRI-safe mode--.
At Column 22, Line number 3, delete "MM-safe mode" and replace with --MRI-safe mode--.
At Column 22, Line number 7, delete "MM-safe mode" and replace with --MRI-safe mode--.